(12) United States Patent
Swann et al.

(10) Patent No.: US 9,050,186 B2
(45) Date of Patent: Jun. 9, 2015

(54) MINIMALLY INVASIVE SURGICAL STABILIZATION DEVICES AND METHODS

(71) Applicant: Conceptus, Inc., Mountain View, CA (US)

(72) Inventors: Betsy Swann, Grass Valley, CA (US); Christopher A. Stout, San Bruno, CA (US); Ken Chan, Richmond, CA (US); Julian Cruzada, San Jose, CA (US); Kathryn A. Tunstall, Napa, CA (US)

(73) Assignee: Bayer Essure Inc., Milpitas, CA (US)

( * ) Notice: Subject to any disclaimer, the term of this patent is extended or adjusted under 35 U.S.C. 154(b) by 0 days.

(21) Appl. No.: 13/748,457

(22) Filed: Jan. 23, 2013

(65) Prior Publication Data

US 2013/0133666 A1  May 30, 2013

Related U.S. Application Data

(60) Division of application No. 11/800,187, filed on May 3, 2007, now Pat. No. 8,360,064, which is a continuation-in-part of application No. 11/165,733, filed on Jun. 24, 2005, now Pat. No. 7,918,863.

(51) Int. Cl.
*A61F 6/06* (2006.01)
*A61F 6/14* (2006.01)
(Continued)

(52) U.S. Cl.
CPC .............. *A61F 6/225* (2013.01); *A61B 17/42* (2013.01); *A61F 6/18* (2013.01); *A61B 1/303* (2013.01); *A61F 6/06* (2013.01); *A61B 1/0014* (2013.01);
(Continued)

(58) Field of Classification Search
CPC .. A61B 17/00; A61B 17/12; A61B 17/12022; A61B 17/3468; A61B 17/42; A61F 5/00; A61F 6/00; A61F 6/06; A61F 6/14; A61F 6/18; A61F 6/20; A61F 6/22; A61F 6/225; A61M 25/00; A61M 25/01; A61M 25/09; A61M 25/09041
USPC ......... 600/100, 104–106, 109–110, 114, 117, 600/160; 606/53, 60, 108, 119, 135; 128/830–831, 833, 839–840
See application file for complete search history.

(56) References Cited

U.S. PATENT DOCUMENTS

| 4,027,510 A | 6/1977 | Hiltebrandt |
|---|---|---|
| 4,245,623 A | 1/1981 | Erb |

(Continued)

FOREIGN PATENT DOCUMENTS

| EP | 0 891 757 A2 | 1/1999 |
|---|---|---|
| GB | 2 021 956 A | 12/1979 |

(Continued)

OTHER PUBLICATIONS

PCT Invitation to Pay Additional Fees, PCT/US2006/012952, date mailed Feb. 2, 2007, total 8 pages.

(Continued)

*Primary Examiner* — Alireza Nia
*Assistant Examiner* — Brandon L Jackson
(74) *Attorney, Agent, or Firm* — Jacob Aikin; James Scheller; Karen B. King

(57) ABSTRACT

The various embodiments of the present inventions provide stabilization devices and methods for use of the stabilization devices with minimally invasive gynecological procedures such as methods of preventing pregnancy by inserting intrafallopian contraceptive devices into the fallopian tubes.

16 Claims, 39 Drawing Sheets

(51) Int. Cl.

| | | |
|---|---|---|
| *A61B 1/00* | (2006.01) | |
| *A61B 1/04* | (2006.01) | |
| *A61F 5/04* | (2006.01) | |
| *A61B 17/56* | (2006.01) | |
| *A61F 11/00* | (2006.01) | |
| *A61B 17/42* | (2006.01) | |
| *A61B 17/46* | (2006.01) | |
| *A61D 1/06* | (2006.01) | |
| *A61F 6/22* | (2006.01) | |
| *A61F 6/18* | (2006.01) | |
| *A61B 1/303* | (2006.01) | |
| *A61B 1/018* | (2006.01) | |
| *A61B 17/00* | (2006.01) | |

(52) U.S. Cl.
CPC ........... *A61B 1/018* (2013.01); *A61B 17/00234* (2013.01); *A61B 2017/00238* (2013.01); *A61B 2017/00336* (2013.01); *A61B 2017/0034* (2013.01)

(56) References Cited

U.S. PATENT DOCUMENTS

| | | | |
|---|---|---|---|
| 4,805,618 | A | 2/1989 | Ueda et al. |
| 4,932,394 | A * | 6/1990 | Nanaumi ............... 600/148 |
| 5,312,415 | A | 5/1994 | Palermo |
| 5,503,320 | A * | 4/1996 | Webster et al. ......... 227/176.1 |
| 5,513,628 | A | 5/1996 | Coles |
| 5,741,292 | A * | 4/1998 | Mendius ............... 606/191 |
| 5,741,320 | A | 4/1998 | Thornton et al. |
| 5,743,904 | A | 4/1998 | Edwards |
| 5,749,889 | A | 5/1998 | Bacich et al. |
| 5,935,137 | A | 8/1999 | Saadat et al. |
| 6,162,196 | A | 12/2000 | Hart et al. |
| 6,261,219 | B1 * | 7/2001 | Meloul et al. ............ 600/3 |
| 6,526,979 | B1 | 3/2003 | Nikolchev et al. |
| 6,634,361 | B1 | 10/2003 | Nikolchev et al. |
| 6,705,323 | B1 | 3/2004 | Nikolchev et al. |
| 6,709,667 | B1 | 3/2004 | Lowe et al. |
| 6,726,682 | B2 | 4/2004 | Harrington |
| 6,740,039 | B1 | 5/2004 | Rafter et al. |
| 6,802,825 | B2 | 10/2004 | Ackerman et al. |
| 6,847,336 | B1 | 1/2005 | Lemelson et al. |
| 6,899,105 | B2 | 5/2005 | Krueger et al. |
| 7,289,139 | B2 | 10/2007 | Amling et al. |
| 7,338,473 | B2 | 3/2008 | Campbell et al. |
| 7,398,780 | B2 | 7/2008 | Callister et al. |
| 7,736,371 | B2 | 6/2010 | Schoepp |
| 2002/0049423 | A1 | 4/2002 | Howell et al. |
| 2002/0072744 | A1 | 6/2002 | Harrington |
| 2003/0009128 | A1 | 1/2003 | Ackerman |
| 2003/0051735 | A1 | 3/2003 | Pavcnik et al. |
| 2003/0105473 | A1 | 6/2003 | Miller |
| 2003/0158464 | A1 | 8/2003 | Bertolero |
| 2003/0206099 | A1 | 11/2003 | Richman |
| 2004/0158127 | A1 | 8/2004 | Okada |
| 2004/0162465 | A1 | 8/2004 | Carrillo |
| 2005/0004512 | A1 | 1/2005 | Campbell et al. |
| 2005/0045184 | A1 | 3/2005 | Khera et al. |
| 2005/0070757 | A1 | 3/2005 | Niwa et al. |
| 2005/0085880 | A1 | 4/2005 | Truckai et al. |
| 2005/0119617 | A1 | 6/2005 | Stecker et al. |
| 2005/0232961 | A1 | 10/2005 | Lowe et al. |
| 2005/0265996 | A1 | 12/2005 | Lentz |
| 2005/0267417 | A1 | 12/2005 | Secrest et al. |
| 2005/0288551 | A1 | 12/2005 | Callister et al. |
| 2006/0116692 | A1 | 6/2006 | Ward |
| 2006/0235433 | A1 | 10/2006 | Secrest et al. |
| 2006/0293560 | A1 | 12/2006 | Nguyen et al. |
| 2007/0088247 | A1 | 4/2007 | Bliweis et al. |
| 2007/0213590 | A1 | 9/2007 | Squicciarini |
| 2008/0154256 | A1 | 6/2008 | Payne et al. |
| 2010/0063360 | A1 | 3/2010 | Harrington et al. |
| 2011/0094519 | A1 | 4/2011 | Gopal et al. |

FOREIGN PATENT DOCUMENTS

| | | | |
|---|---|---|---|
| GB | 2 156 224 | A | 10/1985 |
| WO | WO 99/15116 | | 4/1999 |

OTHER PUBLICATIONS

PCT Notification of Transmittal of International Search Report and the Written Opinion of the International Searching Authority or the Declaration, PCT/US2006/012952, mail date Apr. 27, 2007, total 18 pages.

PCT Notification Concerning Transmittal of International Preliminary Report on Patentability (Chapter 1 of the Patent Cooperative Treaty), and the PCT Written Opinion of the International Searching Authority PCT/US2006/012952, mail date Jan. 10, 2008, total 12 pages.

"Endoscope," Mosby's Medical Dictionary, 8th edition, © 2009, Elsevier, accessed on May 13, 2013 at http://medical-dictionary.thefreedictionary.com/endoscope, 1 pg.

"Hysteroscope," Mosby's Medical Dictionary, 8th edition, © 2009, Elsevier, accessed on May 13, 2013 at http://medical-dictionary.thefreedictionary.com/hysteroscope, 1 pg.

* cited by examiner

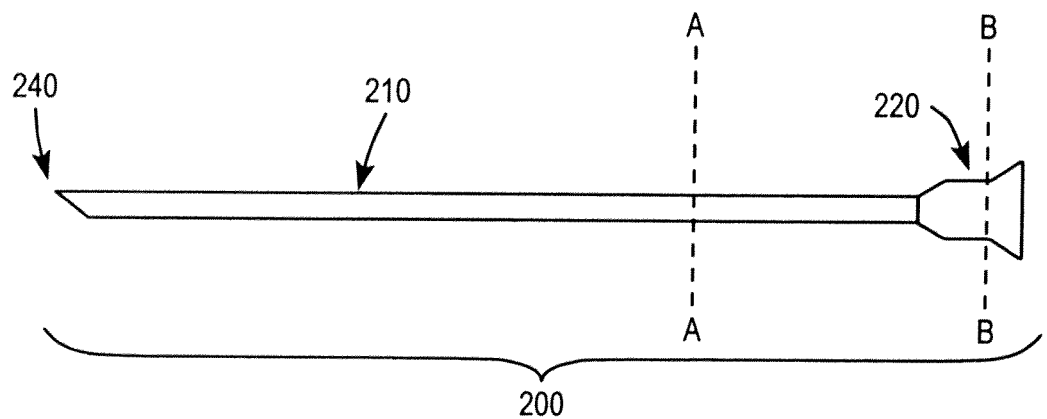
FIG. 2a
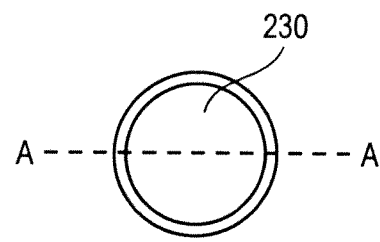
FIG. 2 b
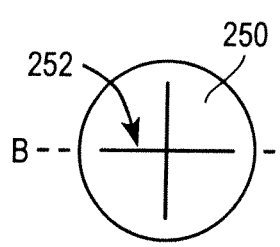 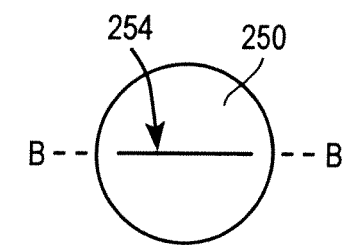 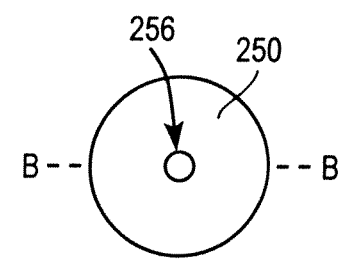
FIG. 2c  FIG. 2d  FIG. 2 e

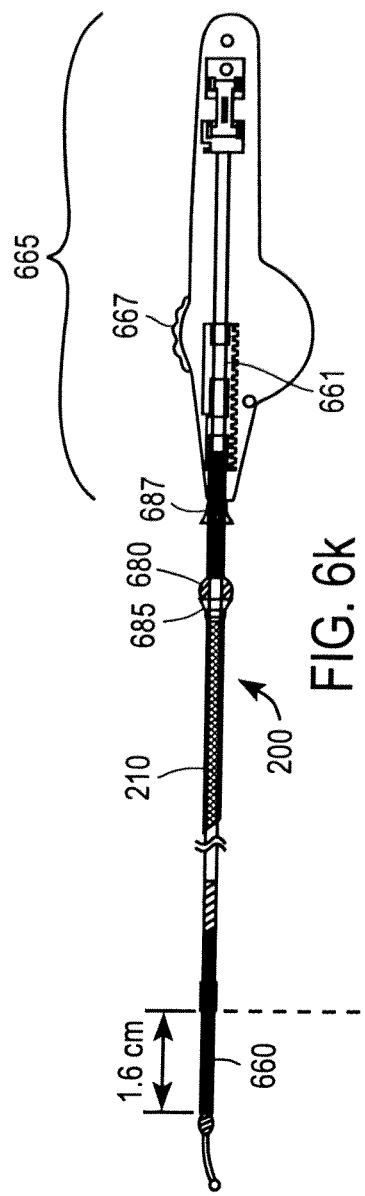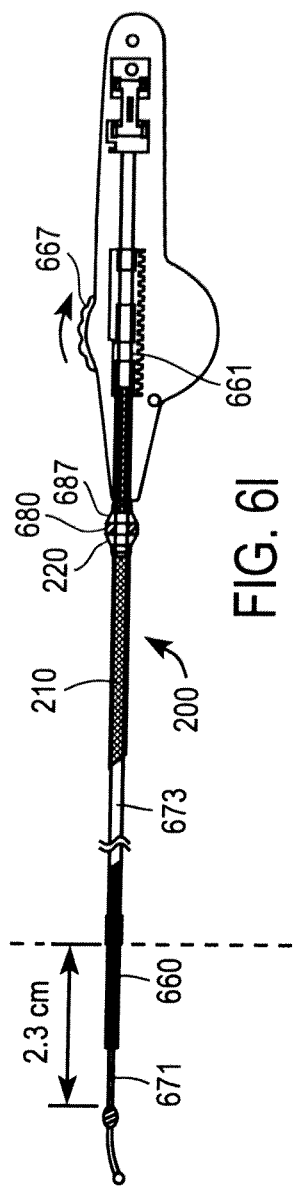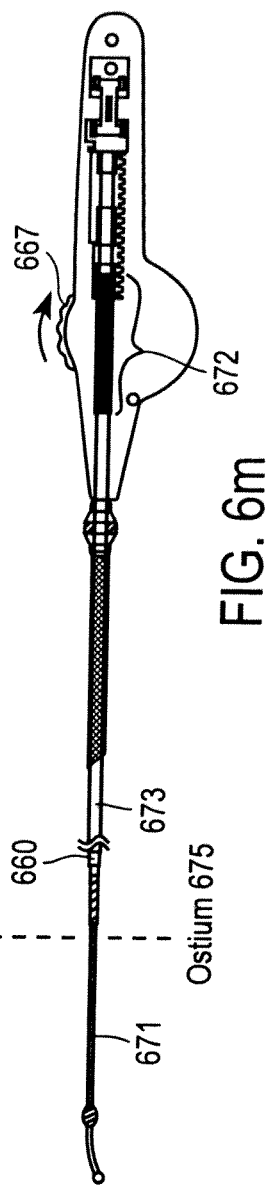

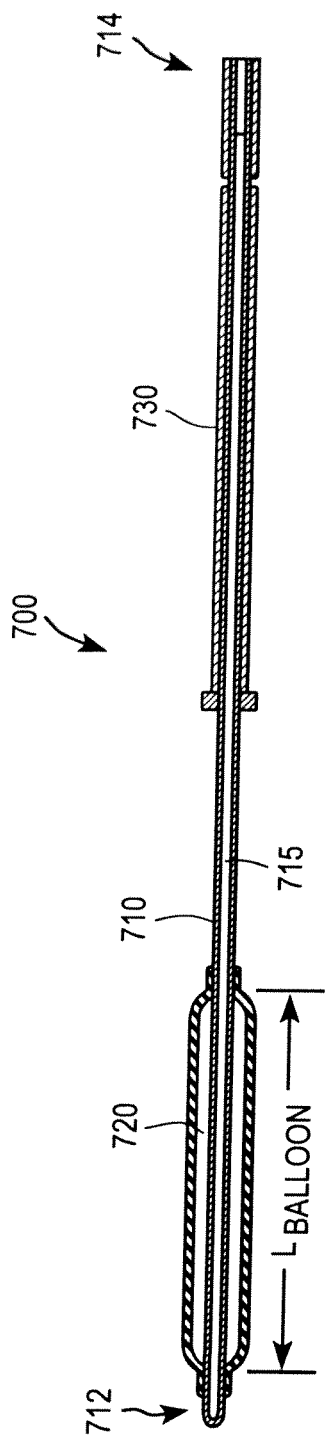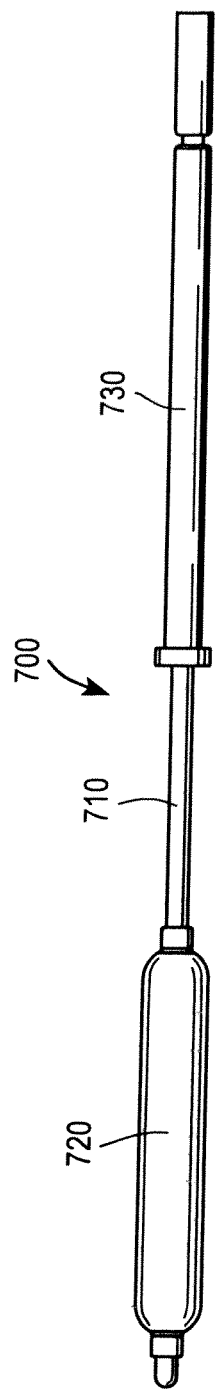
FIG. 7a
FIG. 7b

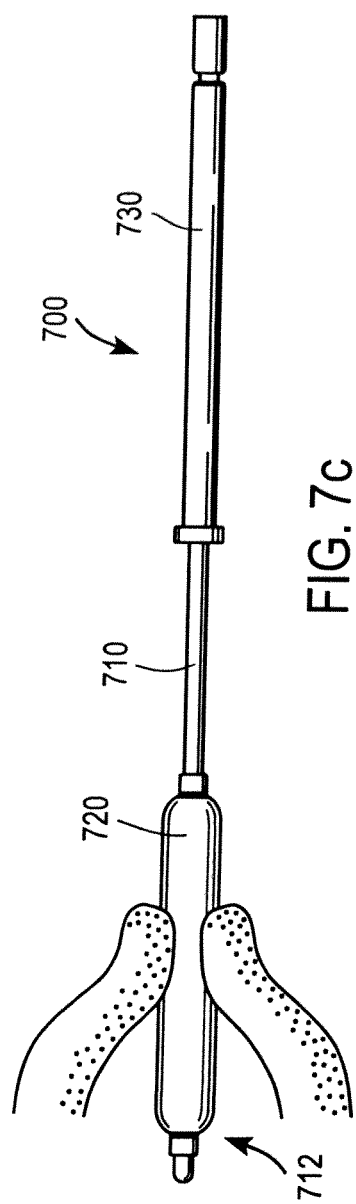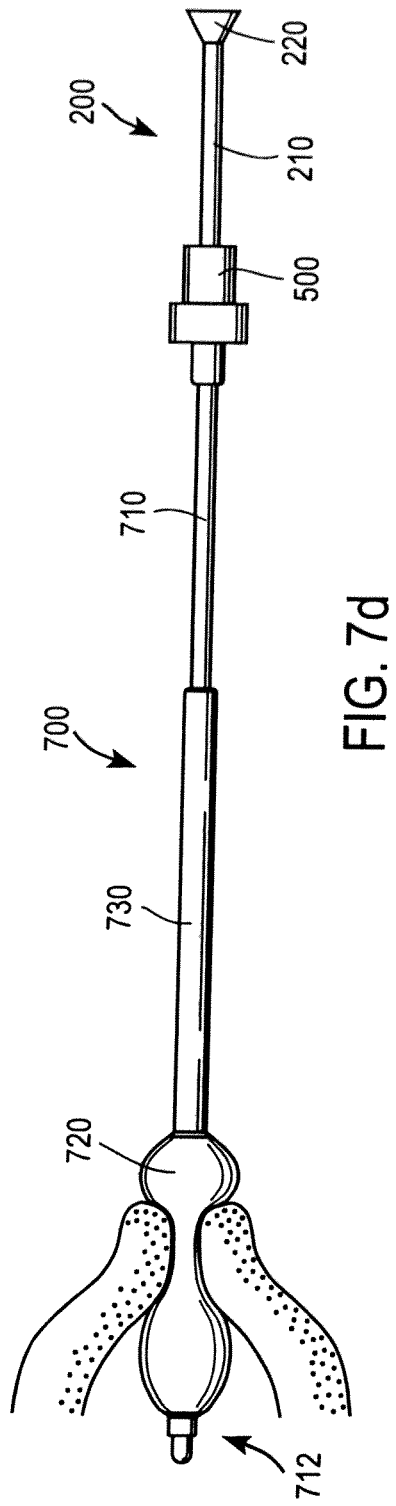
FIG. 7c
FIG. 7d

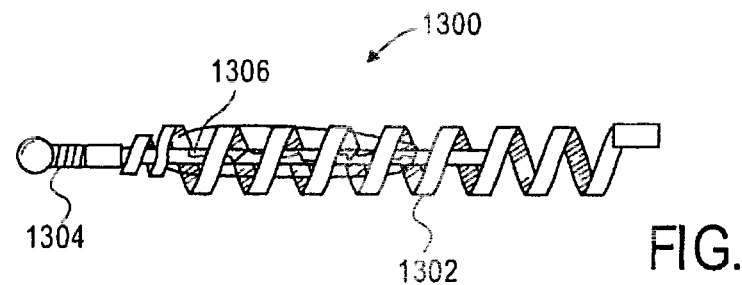
FIG. 13b
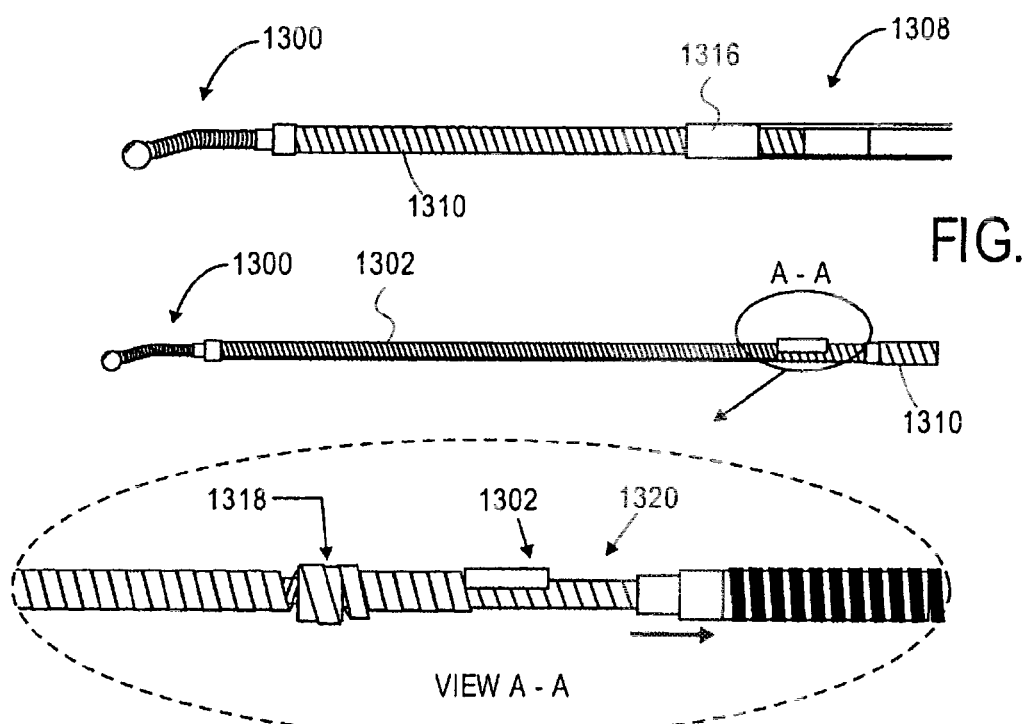
FIG. 13c
FIG. 13d
FIG. 13e

MINIMALLY INVASIVE SURGICAL STABILIZATION DEVICES AND METHODS

RELATED APPLICATIONS

This application is a divisional of U.S. patent application Ser. No. 11/800,187, filed May 3, 2007, which is a continuation-in-part of U.S. patent application Ser. No. 11/165,733, filed on Jun. 24, 2005, entitled "Minimally Invasive Surgical Stabilization Devices and Methods" which has been published as US patent application publication US 2006-0293560 A1, and is hereby incorporated herein by reference in its entirety.

BACKGROUND OF THE INVENTION

1. Field of the Invention

The present invention relates to the field of minimally invasive surgical medical devices and medical procedures. More specifically, the invention relates to devices and methods used for transcervical gynecological procedures.

2. Discussion of Related Art

Female contraception and/or sterilization may be affected by transcervically introducing an object (e.g. a coil) into a fallopian tube to inhibit conception. Devices, systems and methods for such a contraceptive approach have been described in various patents and patent applications assigned to the present assignee. For example, PCT Patent Application No. PCT/US98/20031 published as WO 99/15116 and U.S. Pat. No. 6,526,979 and U.S. Pat No. 6,634,361, and is hereby incorporated herein by reference in its entirety, describe devices that are transcervically inserted into an ostium of a fallopian tube and mechanically anchored within the fallopian tube. The devices described in these patents and patent applications may promote a tissue in-growth around and within the inserted device, which may be referred to as an implant or an insert. One example of such devices is the device known as "Essure" from Conceptus, Inc. of Mountain View, Calif. This tissue in-growth tends to provide long-term contraception and/or permanent sterilization without the need for surgical procedures.

The device used to insert the contraceptive implant into the fallopian tube may be an intrafallopian contraceptive delivery device such as the one illustrated in FIG. 1a.

FIG. 1a illustrates a device similar to the Essure device. The intrafallopian contraceptive delivery device 101 of FIG. 1a is typically formed of a control device, such as a handle 102, a delivery catheter system 103, and a guidewire 104 onto which is held the contraceptive implant to be placed within the fallopian tube. The delivery catheter system 103 contains the guidewire 104, a release catheter (not shown) and the contraceptive implant and the guidewire 104 within the release catheter. The delivery catheter system 103 is transcervically positioned into the uterus and the fallopian tubes via a hysteroscope, such as hysteroscope 100 illustrated in FIG. 1b. The delivery catheter system 103 and guidewire 104 enter the hysteroscope 100 through the working channel 110 of the hysteroscope 100. A distention valve 120 is typically positioned at the tip of the working channel 110. The distention valve 120 seals the entrance of the working channel 110 to prevent a distention fluid, such as saline, to flow out of the hysteroscope 100 as a device, such as the delivery catheter system 103 and guidewire 104 of the intrafallopian contraceptive delivery device 101, is introduced into the working channel 110. The opening 130 into the distention valve 120 is designed to prevent the leakage of any fluid out of the hysteroscope 100 and therefore has the smallest opening possible to allow a very tight fit between the device and the valve opening. To prevent damaging the tip 105 of the guidewire 104 or the contraceptive implant to be inserted into the fallopian tube, the guidewire 104 and delivery catheter system 103 are introduced into the distention valve 120 through an introducer sheath 140. The introducer sheath 140 is formed of a soft flexible material such as plastic or Teflon and has a slit 145 to aid in grasping and in the removal of the introducer sheath 140. The introducer sheath 140 must therefore be inserted into the opening 130 of the distention valve 120 while on a stiff mandrel 150 as illustrated in FIG. 1b. Once the mandrel 150 are placed within the distention valve 120 and the channel 110 to the desired depth the mandrel 150 is removed, leaving the introducer sheath 140 within the working channel 110 and the distention valve 120 as illustrated in FIG. 1c. After placing the introducer sheath 140 into the distention valve 120 the tip 105 of the guidewire 104 and the delivery catheter system 103 may be inserted into the introducer sheath 140 and introduced into the distention valve 120 and the working channel 110 as illustrated in FIG. 1d. The introducer sheath 140 may then be removed. The distention valve 120 may have a tight opening that places pressure on the delivery catheter and causes friction. This friction may make the positioning of the insert within the fallopian tubes difficult. Friction may be created even if the introducer sheath 140 is left within the opening 130 of the distention valve 120. The distention valve 120 prevents fluid leakage from the working channel 110. If an introducer sheath 140 is inserted through the distention valve 120, fluid can spray out of the valve and onto the physician or physician's assistant. The amount of fluid spray-back can be significant depending on the fluid pressure used during the procedure.

Once a physician has positioned the delivery catheter system 103 and the guidewire 104 at a position within the fallopian tube where the contraceptive implant may be deposited, it may be awkward and difficult for the physician to maintain the position and may require the physician to use an assistant to aid in the proper stabilization of the system relative to the hysteroscope.

The contraceptive implant devices in the above references require disengaging from a delivery catheter by using an axial torque. In practice this requires the delivery catheter and endoscope in combination to be fully rotated to disengage a contraceptive implant device from the delivery catheter in order to deposit the contraceptive implant device into a fallopian tube. This maneuver may be difficult and cumbersome to perform considering that the device must remain axially aligned in the fallopian tube.

SUMMARY OF THE DESCRIPTION

Various different embodiments are disclosed below and the following summary provides a brief description of only some of these embodiments. According to one aspect of the invention, certain embodiments described below relate to a medical device to stabilize a device for a minimally invasive gynecological procedure with respect to a device that provides a transcervical pathway. The device for the minimally invasive gynecological procedure may be an intrafallopian contraceptive delivery device. The device that provides a transcervical pathway may be a hysteroscope or a catheter. In an embodiment, the stabilization device may maintain a fixed longitudinal distance between an intrafallopian contraceptive device and a hysteroscope. The stabilization device may include a port for the insertion of a catheter to deliver a topical anesthetic or a contrast media to a patient during a minimally invasive gynecological procedure. The stabilization device may include a handle for manipulating a hysteroscope. Further embodiments describe methods of stabilizing the device for the minimally invasive gynecological procedure with respect to the device that provides a transcervical pathway using a stabilization device.

The minimally invasive gynecological procedure may include coupling a handle of a catheter to an endoscope. The procedure may include inserting a sterilization device coupled to a distal portion of the catheter into a fallopian tube of the patient, the sterilization device having an outer expandable portion. The procedure may include activating the outer expandable portion of the sterilization device to expand inside the fallopian tube. The procedure may include decoupling a catheter from an expanded sterilization device while keeping the endoscope and catheter in a stable position rotationally relative to the patient. The procedure may include using a stabilization device to limit depth of insertion of a sterilization device.

The minimally invasive gynecological procedure may be part of a system which may include a stabilization arm coupled on an endoscope. The system may include a wireless camera coupled to an endoscope. The wireless camera may capture an image or a sequence of images of an ostium of a fallopian tube and transmit that image or sequence of images to a wireless receiver which provides the image or sequence of images to a display. The system may include a catheter configured for a transcervical medical procedure coupled to an endoscope.

Various other devices and methods for using devices, including kits for use in treating patients, are also described below. Other features of the present invention will be apparent from the accompanying drawings and from the detailed description that follows.

BRIEF DESCRIPTION OF THE DRAWINGS

FIG. 2a is an illustration of a side view of a stabilization device formed of a sleeve and a mechanical means for coupling the proximal end of the stabilization device to a control device of a device for a gynecological procedure.

FIG. 2b is an illustration of a cross-sectional view of the sleeve of the stabilization device of FIG. 2a.

FIG. 2c is an illustration of a cross-sectional view of a transverse membrane within the stabilization device of FIG. 2a having a cross-hatched opening.

FIG. 2d is an illustration of a cross-sectional view of a transverse membrane within the stabilization device of FIG. 2a having a slit opening.

FIG. 2e is an illustration of a cross-sectional view of a transverse membrane within the stabilization device of FIG. 2a having a hole opening.

FIG. 5b is an illustration of a cross-sectional view of the distention valve of FIG. 5a.

FIG. 7a illustrates a cut-away side view of an access catheter.

FIG. 7b illustrates a side view of the outside surface of an access catheter.

FIG. 7c illustrates a side view of an access catheter that has been positioned within the cervix.

FIG. 7d illustrates a side view of the access catheter once the balloon on its distal end has been expanded to fix the position of the access catheter within the cervix.

FIG. 13b is a side view of a sterilization device in an expanded configuration.

FIGS. 13c, 13d, and 13e show side views of a sterilization device in an non-expanded configuration coupled to a delivery catheter.

DETAILED DESCRIPTION OF THE PRESENT INVENTION

Figure 1A:
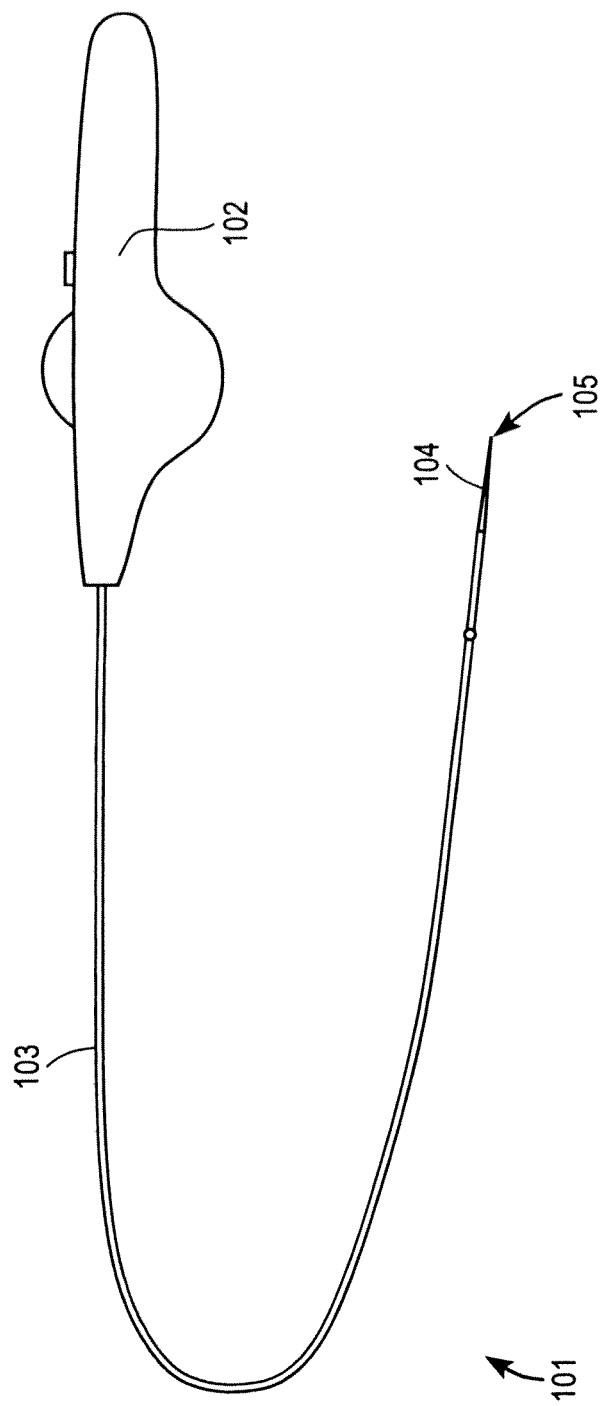
FIG. 1a is an illustration of an intrafallopian contraceptive delivery device.
Figure 1:
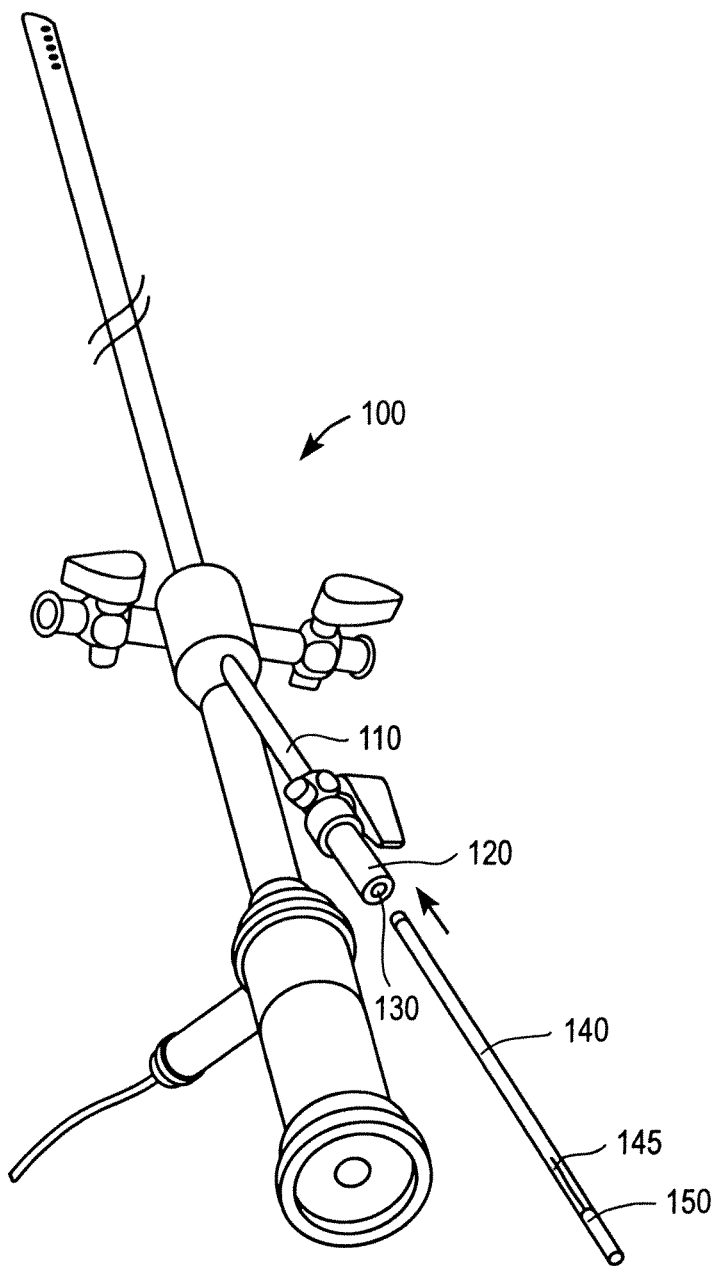
FIG. 1b is an illustration of a hysteroscope and an introducer sheath on a mandrel designed for insertion into a distention valve of a hysteroscope.
FIG. 1c is an illustration of the hysteroscope of FIG. 1b after the introducer sheath has been inserted into the distention valve of the hysteroscope.
FIG. 1d is an illustration of a delivery catheter of an intrafallopian contraceptive delivery device before its insertion into the introducer sheath and hysteroscope.
FIG. 1e is an illustration of a delivery catheter of an intrafallopian contraceptive delivery device after its insertion into the hysteroscope and the removal of the introducer sheath.
Figure 1:
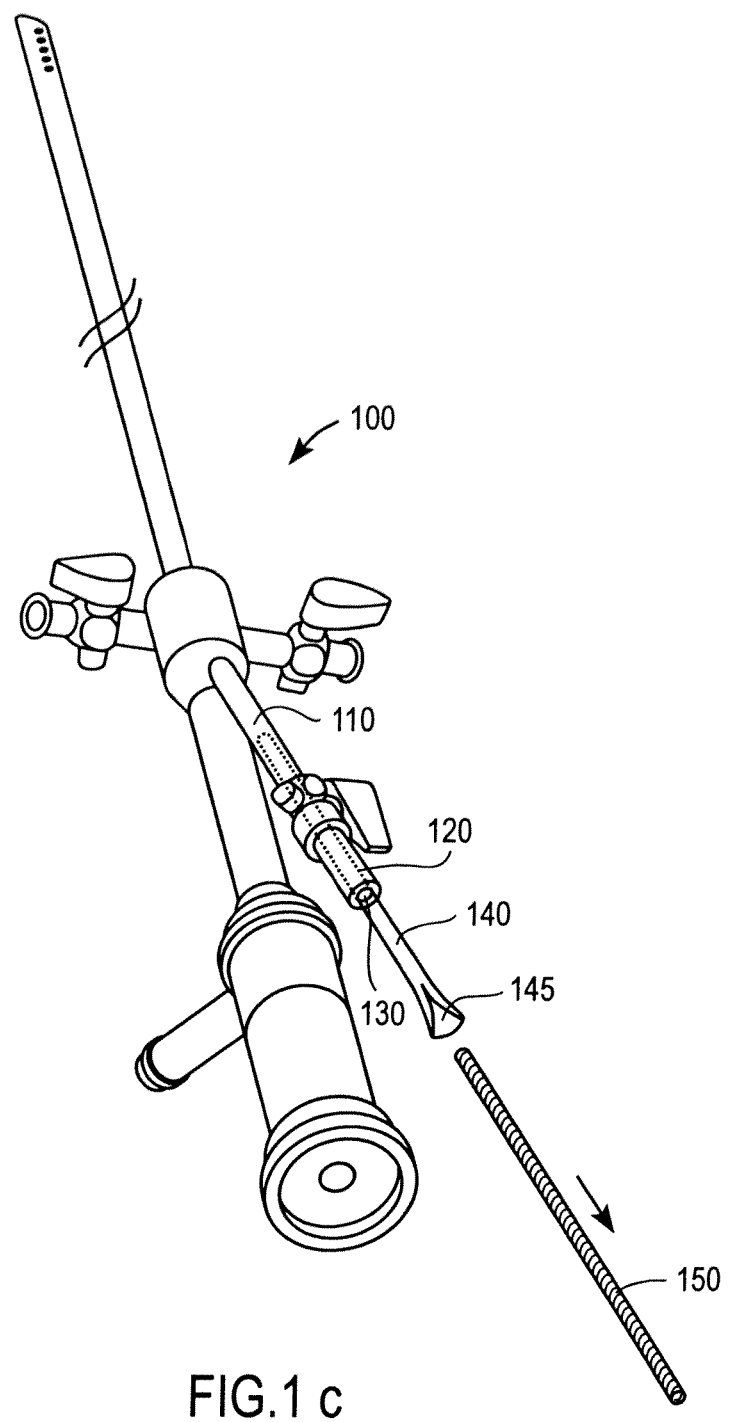
Figure 1:
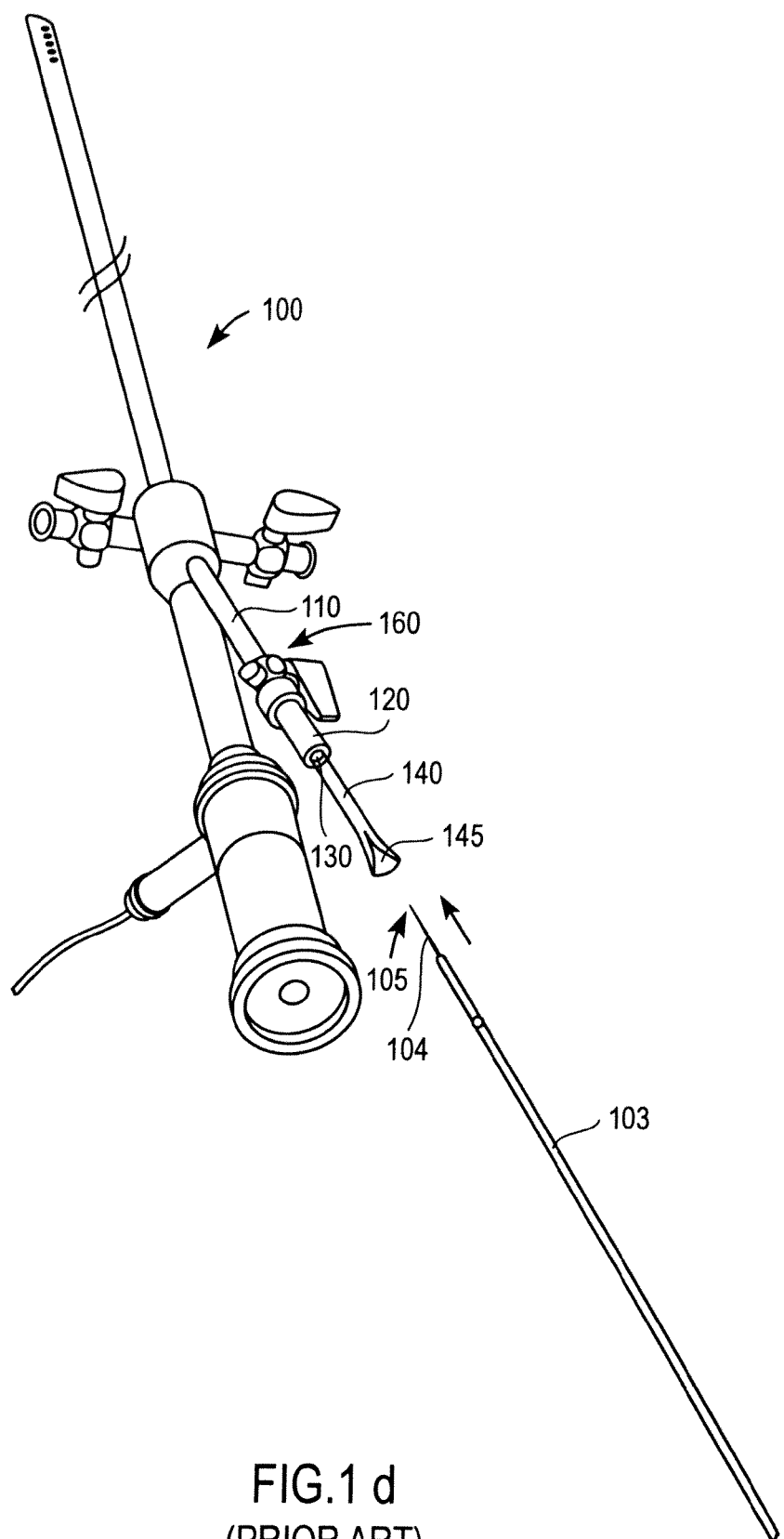
Figure 1:
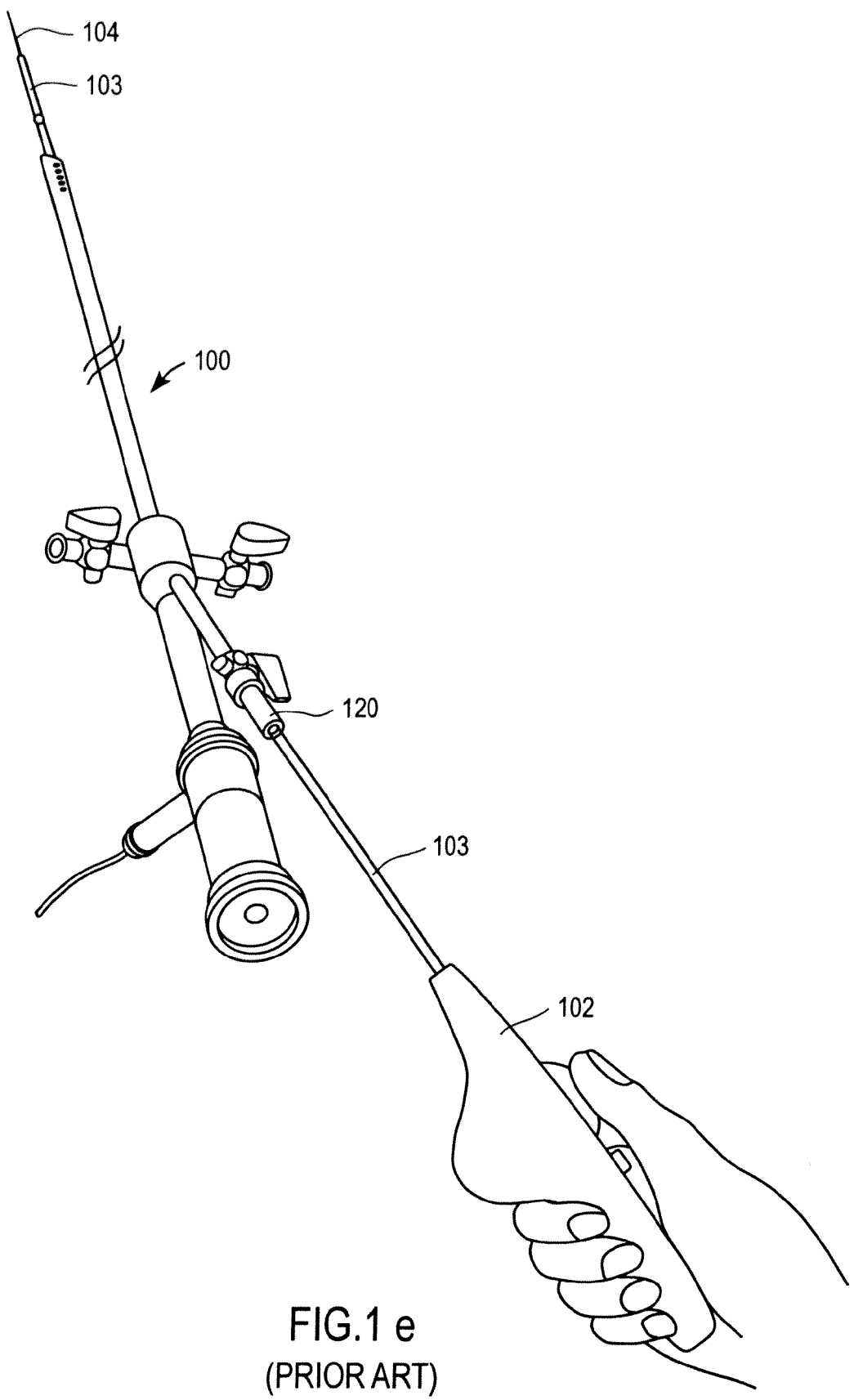

The subject invention will be described with reference to numerous details set forth below, and the accompanying drawings will illustrate the invention. The following description and drawings are illustrative of the invention and are not to be construed as limiting the invention. Numerous specific details are described to provide a thorough understanding of the present invention. However, in certain instances, well-known or conventional details are not described in order to not unnecessarily obscure the present invention in detail.

The various embodiments of the present inventions provide stabilization devices and methods for use of the stabilization devices with minimally invasive gynecological procedures such as methods of preventing pregnancy by inserting intrafallopian contraceptive devices into the fallopian tubes, the removal of uterine polyps, endometrial ablation, cryotherapy of the uterus, myomectomy, radiologic fibroid embolization, uterine and vaginal relaxation, female urological disorders, dilation and curettage, endometrial biopsy, colposcopy, hysterosalpinograpy, excision of submucous myoma, polypectomy or intrauterine adhesions, laparoscopy, minilaparoscopy, surgery for urinary incontinence, reconstructive pelvic procedure, treatment for infertility such as renastamosis, selective salpingectomy, salpingostomy, fibrioplasty, and tubal cannulation. The intrafallopian contraceptive devices may provide permanent contraception or sterilization. Examples of contraceptive devices and method for using these devices with delivery systems are provided in U.S. Pat. No. 6,526,979 and U.S. Pat. No. 6,634,361, both of which are incorporated herein by reference as well as other types of contraceptive devices which may employ other structures. It is to be understood that embodiments of the current invention may also be used with non-gynecological minimally invasive surgeries that employ endoscopes. Examples of non-gynecological minimally invasive surgeries include angioscopy, arthroscopy, bronchoscopy, cystoscopy, solonoscopy, systourethroscopy, esophagogastroduodenoscopy, gastroscopy, largyngoscopy, protosigmoidoscopy, rhinolaryngoscopy, subfacial edoscopic perforating vein surgery, and sigmoidoscopy.

The delivery systems for the intrafallopian contraceptive devices are generally formed of a catheter containing the contraceptive device or devices and a handle that is used to control the placement of the catheter. The intrafallopian contraceptive devices may be positioned by the retraction of the catheter to expose the contraceptive device and the deposition of the contraceptive device within the fallopian tube. The stabilization devices are adapted to be coupled to a control device of an intrafallopian contraceptive delivery device, such as the handle of the delivery systems described in the above-referenced patents, and to a device that provides a pathway through the cervix to maintain a fixed longitudinal distance between the control device and the device that provides a pathway through the cervix. This device may free up one of the hands of a physician performing the procedure by maintaining the fixed distance between the control device and an endoscope. Examples of endoscopes include a hysteroscope, an angioscope, an arthroscope, a bronchoscope, a choledochoscope, a colonoscope, a colposcope, a cystoscope, a cystourethroscope, a duodenoscope, an esophagoscope, an esophagogastroduodenoscope, a falloposcope, a gastroscope, a laryngoscope, a laparoscope, a mini-laparoscope, an ostoscope, an opthalmoscope, a proctoscope, a proctosigmoidoscope, a sigmoidoscope, and a thoracoscope.

In an embodiment, the endoscope may be a hysteroscope for gynecological procedures such as the placement of the contraceptive devices within the fallopian tubes. The accuracy of the placement of the contraceptive devices within the fallopian tubes may be increased due to the greater stabilization and the standardization of the longitudinal distance between the control device and the hysteroscope. In an embodiment, the stabilization device may also facilitate the delivery of a topical anesthetic to the cervix and the uterus. In another embodiment, the stabilization device may facilitate the delivery of a contrast media into the uterus for ultrasound or radiography.

The stabilization device is formed of a means for coupling the stabilization device to a device for a minimally invasive gynecological procedure and of a means for coupling the stabilization device to a device that provides a transcervical pathway. The device that provides a transcervical pathway may be a hysteroscope or a catheter, for example. By coupling the stabilization device to both the device for the minimally invasive gynecological procedure and the device that provides a transcervical pathway, the stabilization device may stabilize the position of the device for the minimally invasive gynecological procedure with respect to the device that provides a transcervical pathway. The stabilization of these devices with respect to one another may facilitate the ease with which the gynecological procedures are performed as well as increase the accuracy of the gynecological procedures. For example, the stabilization device may be adapted to be coupled to an intrafallopian contraceptive delivery device and to a hysteroscope to maintain a fixed longitudinal distance between the intrafallopian contraceptive device and the hysteroscope.

In one embodiment, the stabilization device may be a sleeve such as the one illustrated in FIG. 2a. FIG. 2a illustrates a stabilization device 200 formed of a sleeve 210 and a means 220 for coupling the stabilization device to a control device of an intrafallopian contraceptive device. The sleeve 210 may be formed of a material having a stiffness sufficient to stabilize the control device with respect to the hysteroscope. Any hysteroscope that is capable of performing the methods described herein may be used, but in particular embodiments the hysteroscope may be an Olympus Storz Bettocchi, a Wolf, a Wolf 45° "Panoview Plus", or a Circon ACMI. The material used to form the sleeve 210 may be a metal such as stainless steel or nitinol or a material such as polycarbonate or PEEK (polyetheretherketone). The sleeve 210 may also be coated with a soft polymer coating to increase the ability of the ball valve within the channel of the hysteroscope to grip the stabilization device 200 and to hold it in place. The sleeve may have a length in the approximate range of 1 cm and 150 cm, and more particularly in the range of 3.5 cm and 12.0 cm. The length of the sleeve may vary depending on the use. In an embodiment, the sleeve may have a length sufficient to extend through a working channel of a hysteroscope. In another embodiment the sleeve may have a length sufficient to extend through the entire length of a hysteroscope. In an alternate embodiment, the sleeve may have a length sufficient to reach the fallopian tubes through a device that provides a transcervical pathway, such as a catheter.

The sleeve 210 has a lumen 230 extending longitudinally through the entire sleeve. The lumen 230, as illustrated in a cross-section A-A in FIG. 2b, has a diameter large enough to fit around a catheter that is part of a delivery device for an intrafallopian contraceptive device. This is to prevent friction between the sleeve 210 and the delivery catheter during insertion of the delivery catheter and guide wire and during retraction of the delivery catheter. In an embodiment, the diameter of the lumen 230 may be in the approximate range of 2 French and 9 French, and in another embodiment may have a diameter of approximately 5 French. The distal end 240 of the stabilization device 200 may be tapered as illustrated in FIG. 2a to enable the distal end to be fitted into a distention valve of a hysteroscope. The selection of the shape of the distal end 240 of the stabilization device 200 may be influenced by the shape of the opening into the rubber-like material of the distention valve as well as the stiffness of the rubber-like material that forms the distention valve. A tapered distal end 240 of the stabilization device 200 may be valuable for insertion of the stabilization device 200 into a stiff or tight opening in the distention valve. In an alternate embodiment the distal end 240 of the stabilization device 200 may be blunt, such as in embodiments where the distention valve is part of the stabilization device 200. The means for coupling the stabilization device to the device that provides a transcervical pathway, such as the control device of an intrafallopian contraceptive device, may be a mechanical fitting such as that illustrated in FIG. 2a at the proximal end of the sleeve 210. The mechanical fitting 220 may include a transverse membrane 250 to prevent the backflow of fluid from the hysteroscope from spilling out onto the operator and the control device of the intrafallopian contraceptive delivery device. The transverse membrane 250 is illustrated in FIGS. 2c, 2d, and 2e as the B-B cross-section of the mechanical fitting 220. The transverse membrane 250 is formed with an opening through which the catheter of the intrafallopian contraceptive delivery device can fit. The opening in the transverse membrane forms a seal around the catheter to prevent the backflow of fluid. The opening may be a crosshatch seal 252 as illustrated in FIG. 2c, a slit seal as illustrated in FIG. 2d, or a hole seal as illustrated in FIG. 2e. In alternate embodiments the transverse membrane 250 may be a double membrane having different or the same combinations of the various types of seals. For example, the double membrane may be a combination of a slit seal and a hole seal, a hole seal and a slit seal, a hole seal and a crosshatch seal. The seal combinations of the double membrane may also vary with respect to which seal is distal and which seal is proximal.

Figure 2F:
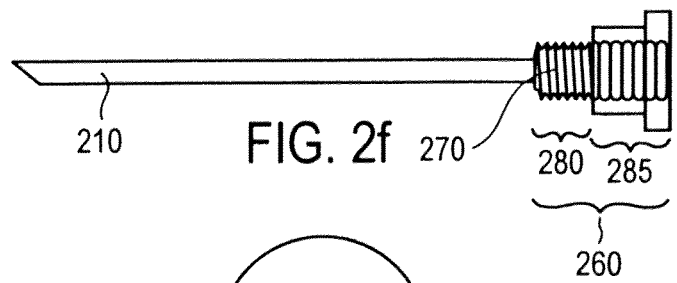
FIG. 2f is an illustration of a side view of a stabilization device formed of a sleeve and an adjustable O-ring for coupling the proximal end of the stabilization device to a device for a gynecological procedure.
Figure 2G:
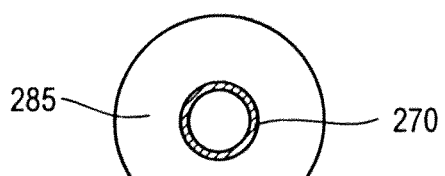
FIG. 2g is an end-on view of the proximal end of the adjustable O-ring in an open position.
Figure 2H:
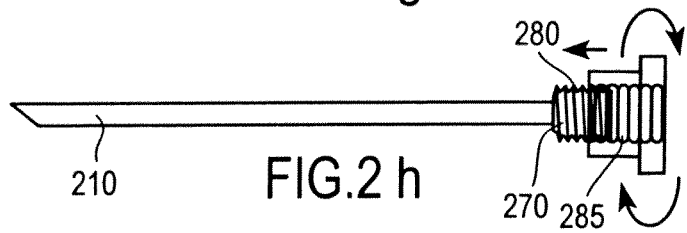
FIG. 2h is a side view of the stabilization device of 2f after screwing down the adjustable O-ring to partially close the O-ring.
Figure 2I:
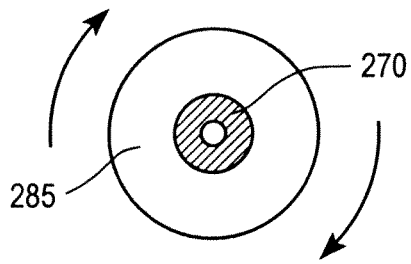
FIG. 2i is an end-on view of the proximal end of the partially closed adjustable O-ring of FIG. 2h.
Figure 2J:
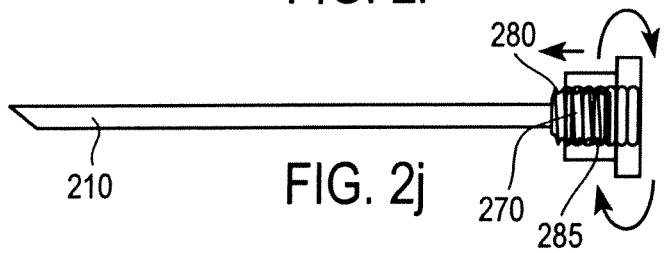
FIG. 2j is a side view of the stabilization device of FIG. 2h after further screwing down the adjustable O-ring to close the O-ring.
Figure 2K:
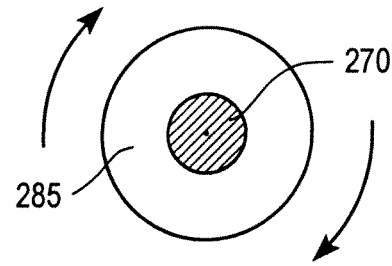
FIG. 2k is an end-on view of the distal end of the closed adjustable O-ring of FIG. 2j.

In an alternate embodiment, the means for coupling the stabilization device 200 to the delivery catheter of a device for a minimally invasive gynecological procedure, such as an intrafallopian contraceptive delivery device, may be an adjustable O-ring 260 such as that illustrated in FIGS. 2f-2k. FIGS. 2f and 2g illustrate the adjustable O-ring 260 in a fully open position. The adjustable O-ring is formed of an O-ring within a first sleeve 280. The outer surface of the first sleeve 280 has screw threads that are threaded by the screw threads inside the second sleeve 285. In the fully open position, the second sleeve 285 has not been screwed onto the first sleeve 280. FIGS. 2h and 2i illustrate the adjustable O-ring after the second sleeve 285 has been screwed onto the first sleeve 280 to reduce the diameter of the O-ring 270. Continuing to screw the second sleeve 285 onto the first sleeve 280 will seal closed the O-ring 270 completely, as illustrated in FIGS. 2j and 2k.

The adjustable O-ring may be adjusted to form a seal around a delivery catheter to hold the stabilization device 200 in place. The seal also serves to prevent backflow of fluid from the hysteroscope out of the stabilization device 200.

Figure 2L:
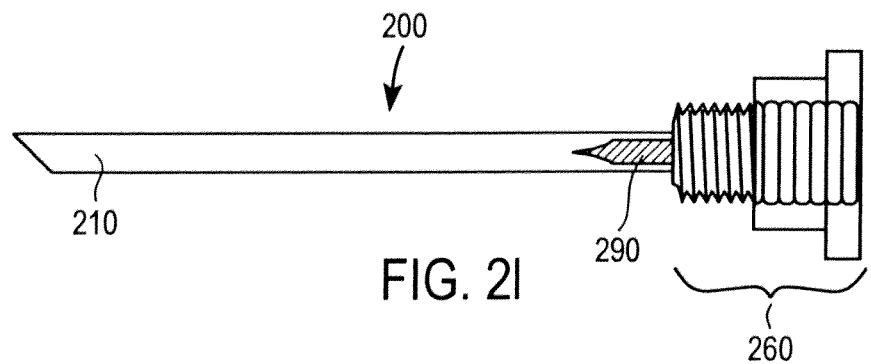
FIG. 2l is an illustration of a side view of a stabilization device formed of a sleeve, an adjustable O-ring, and a duckbill valve.
Figure 2M:
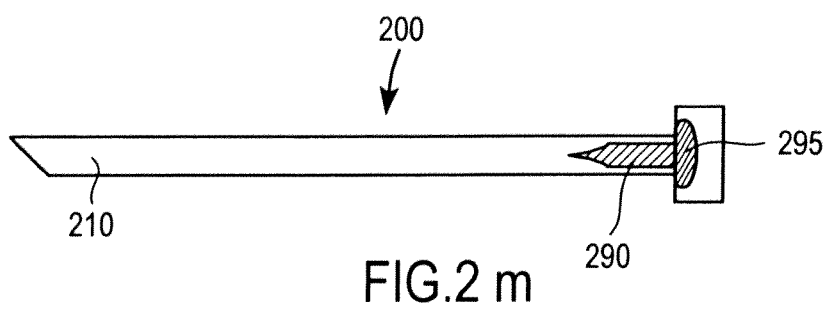
FIG. 2m is an illustration of a side view of a stabilization device formed of a sleeve, an O-ring, and a duckbill valve.
Figure 2N:
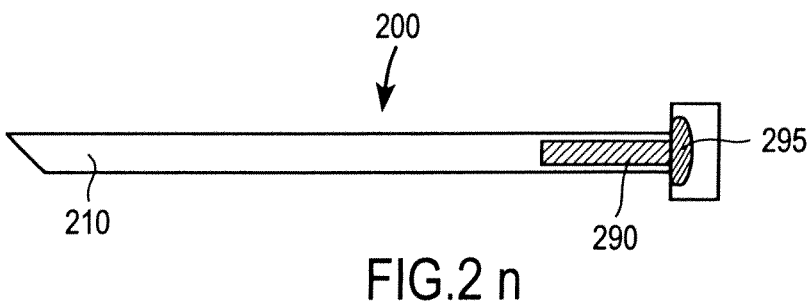
FIG. 2n is an illustration of a top view of the duckbill valve of FIG. 2m.
Figure 2O:
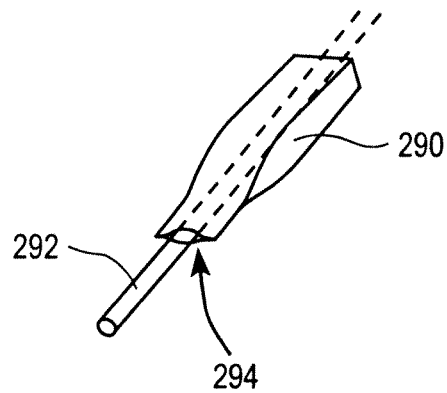
FIG. 2o is an illustration of a detailed view of the duckbill valve of FIGS. 2l-2n through which a catheter has been inserted.

As illustrated in FIG. 2l, the stabilization device may further include a duckbill valve 290. The duckbill valve 290 may be coupled to the adjustable O-ring 260 at the proximal end of the sleeve 210 to form a continuous lumen with the adjustable O-ring 260. The duckbill valve 290 may provide a further seal to prevent the backflow of fluid out of stabilization device 200, particularly when tightening the adjustable O-ring 260 onto a delivery catheter. The duckbill valve 290 may also be used in combination with a non-adjustable O-ring 295. FIG. 2m illustrates a side-view of the duckbill valve 290 in combination with the non-adjustable O-ring 295. FIG. 2n illustrates a top-view of the duckbill valve 290 in combination with the non-adjustable O-ring 295. The non-adjustable O-ring 295 may have an opening having a diameter sufficient to form a seal around a delivery catheter. In this embodiment, the duckbill valve 290 also serves to further prevent the backflow of fluid out of the stabilization device 200. The non-adjustable O-ring 295 may also be used alone, without the duckbill valve 290, as a means for coupling the stabilization device 200 to a device for a gynecological procedure. A detailed view of the duckbill valve 290 is illustrated in FIG. 2o. FIG. 2o illustrates a catheter 292 through a lumen in the center of the duckbill valve 290. The catheter 292 exits the duckbill valve 290 through a slit seal 294 at the distal end (the duckbill) of the duckbill valve 290. Because the duckbill valve 290 is formed of a flexible rubber-like material the slit seal 294 of the duck bill valve 290 forms a seal around the catheter 292.

Figure 3A:
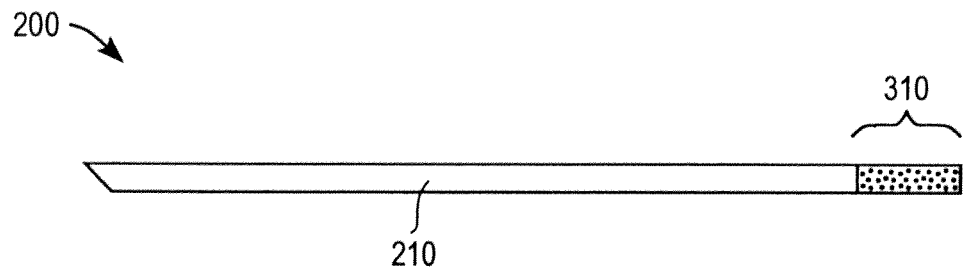
FIG. 3a is an illustration of a side view of a stabilization device formed of a sleeve and of a textured friction fitting.
Figure 3B:
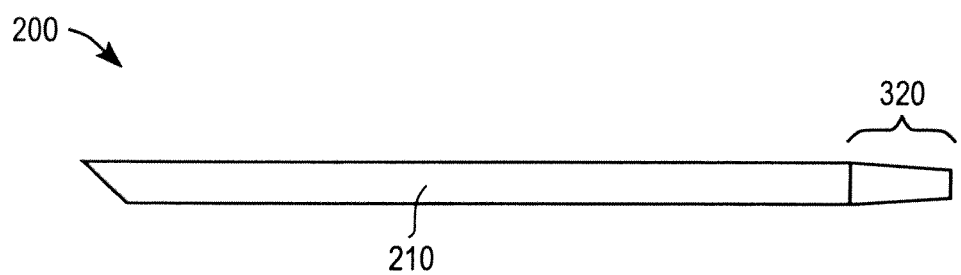
FIG. 3b is an illustration of a side view of a stabilization device formed of a sleeve and of a tapered friction fitting.
Figure 3C:
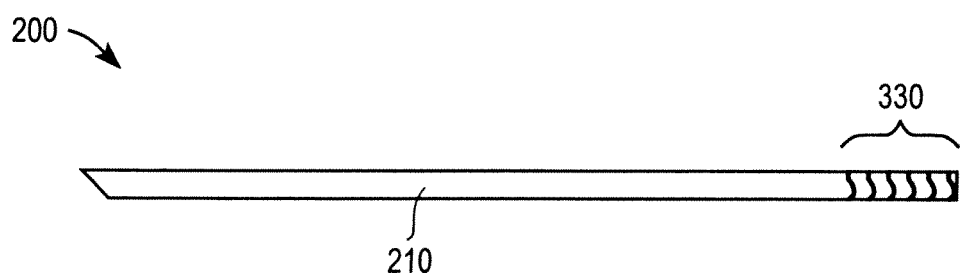
FIG. 3c is an illustration of a side view of a stabilization device formed of a sleeve and of a screw fitting.

The means for coupling the stabilization device 200 to the control device of the intrafallopian contraceptive delivery device may alternatively be a friction fitting that is designed to fit into a control device of a device for a gynecological procedure, such as the handle of an intrafallopian contraceptive delivery device. The friction fitting may be formed as a textured portion 310 on the distal end of the sleeve 210 as illustrated in FIG. 3a, as a portion of the sleeve 210 with a more narrow diameter 320 as illustrated in FIG. 3b, or a portion of the sleeve 210 having a screw thread 330 as illustrated in FIG. 3c.

Figure 4A:
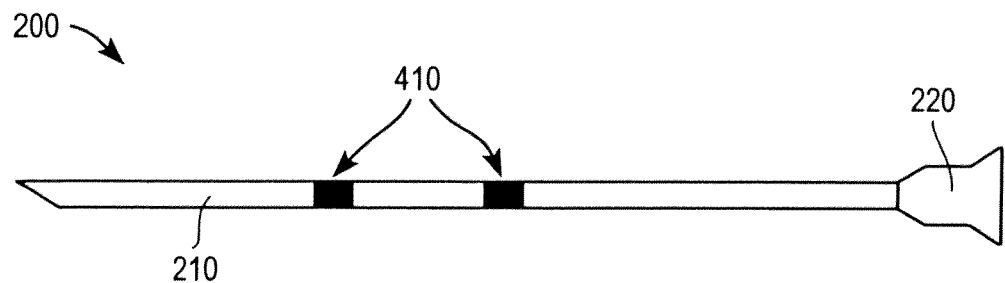
FIG. 4a is an illustration of a side view of a stabilization device having a first marker and a second marker on the outside of the sleeve.
Figure 6A:
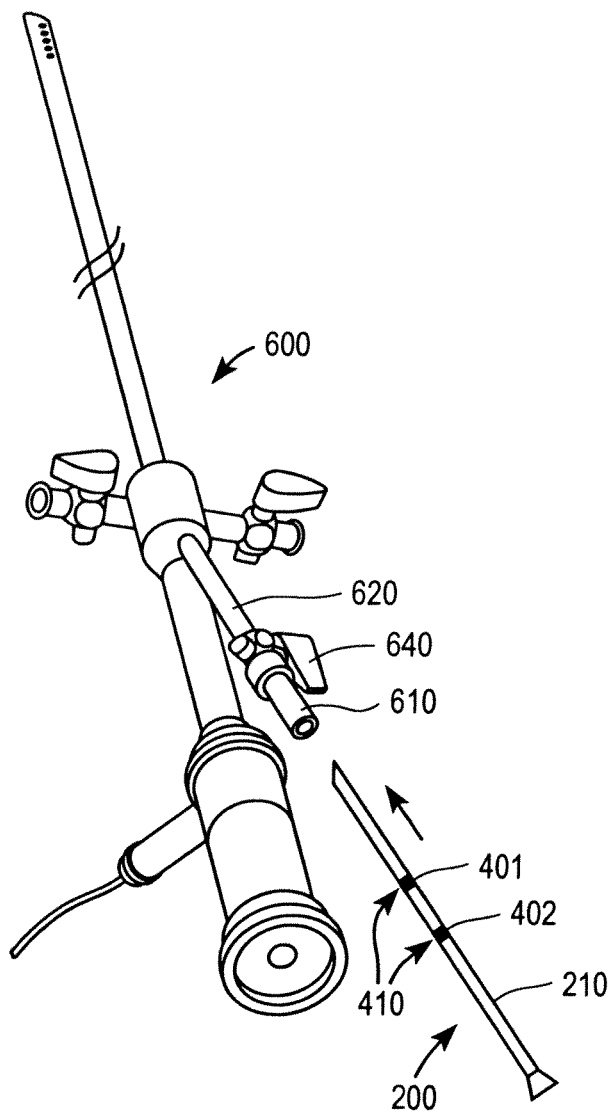
FIG. 6a illustrates a hysteroscope and a stabilization device positioned for insertion into the distention valve of the hysteroscope.
Figure 6B:
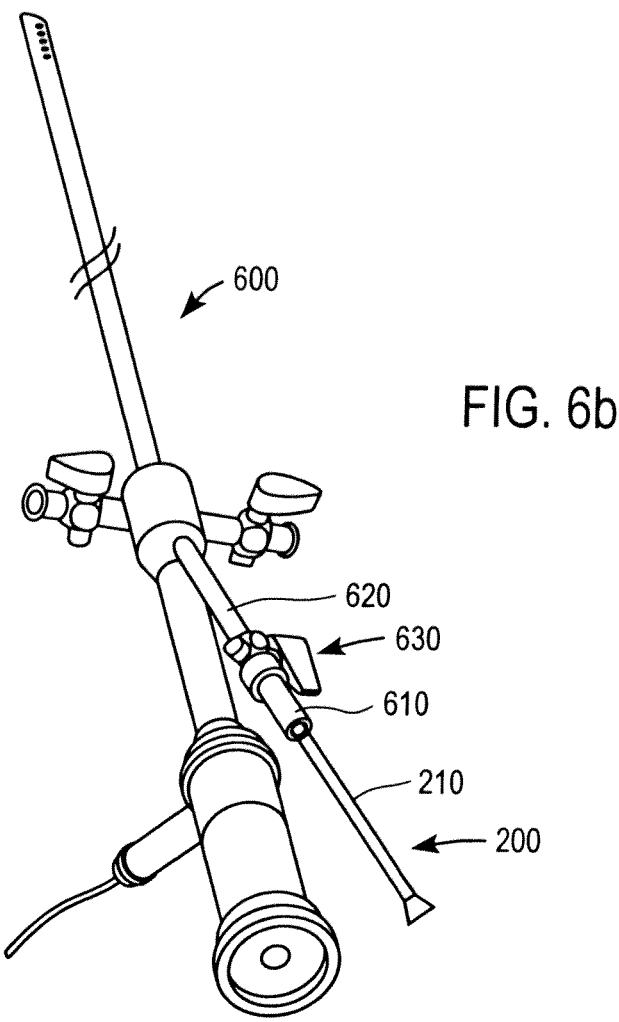
FIG. 6b illustrates a stabilization device inserted into a distention valve and a channel of the hysteroscope.
Figure 6C:
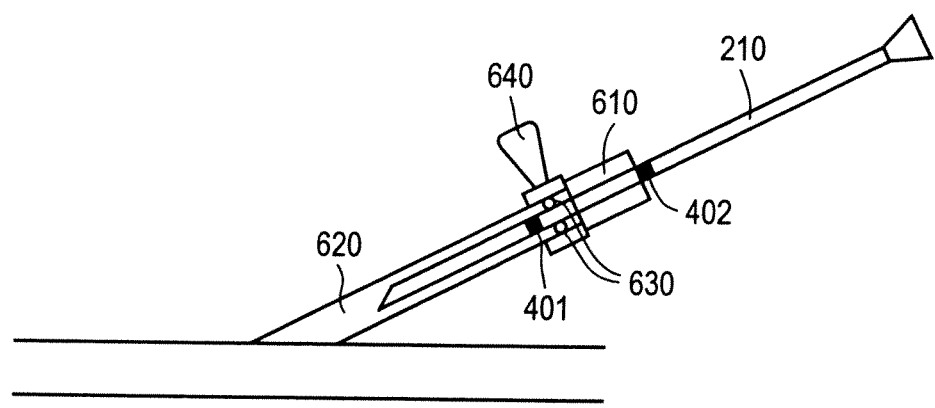
FIG. 6c illustrates a cut-away side view of the stabilization device within the distention valve and channel of the hysteroscope.
Figure 6:
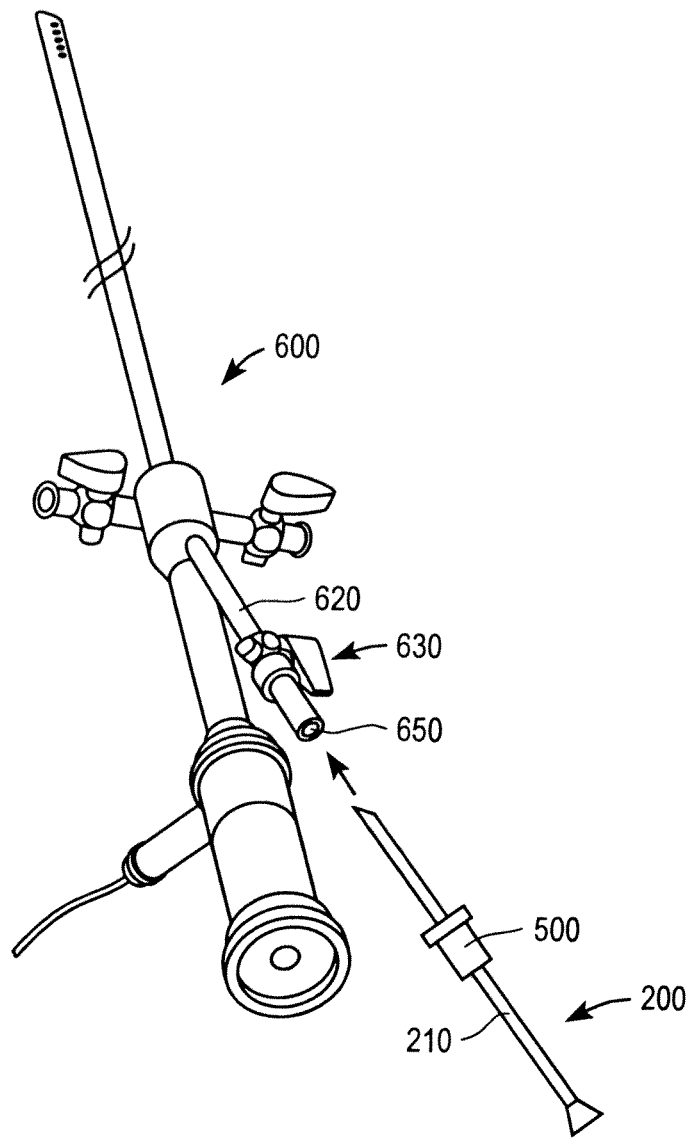
FIG. 6d illustrates a stabilization device having a distention valve positioned for insertion into the working channel of a hysteroscope.
FIG. 6e illustrates a stabilization device having a distention valve and a length sufficient to reach beyond the end of the hysteroscope.
FIG. 6f illustrates a stabilization device inserted into a hysteroscope and a delivery catheter of an intrafallopian contraceptive delivery device inserted into the stabilization device and the hysteroscope.
FIG. 6g illustrates a stabilization device coupled to both a hysteroscope and a control device of an intrafallopian contraceptive delivery device.
FIG. 6h illustrates a stabilization device coupled to the delivery catheter of an intrafallopian delivery device by an adjustable O-ring.
FIG. 6i illustrates a stabilization device having a mechanical fitting designed to couple to an adaptor on the end of the control device of an intrafallopian contraceptive delivery device.
FIG. 6j illustrates the stabilization device of FIG. 6h coupled to the adaptor on the end of the control device of the intrafallopian contraceptive delivery device.
FIG. 6k illustrates a cut-away side view of a handle of an intrafallopian contraceptive delivery device before tracking forward the delivery catheter.
FIG. 6l illustrates a cut-away side view of a handle of an intrafallopian contraceptive delivery device after tracking forward the delivery catheter.
FIG. 6m illustrates a cut-away side view of a handle of an intrafallopian contraceptive delivery device.
Figure 6E:
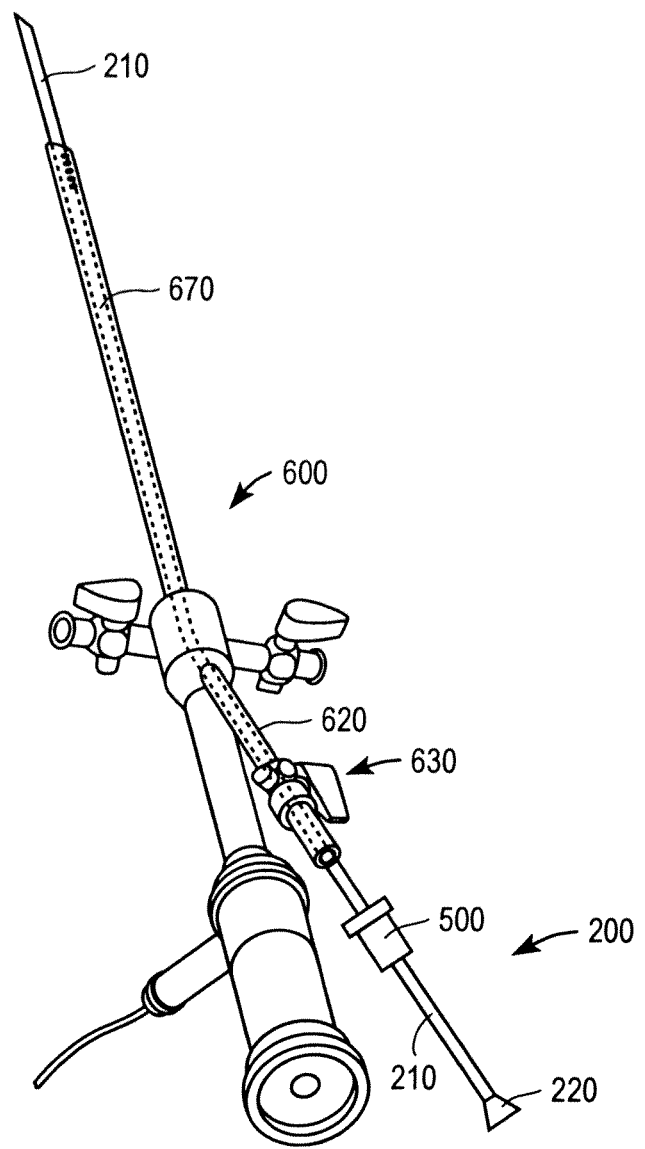

In another embodiment, the stabilization device of FIG. 2a may have an insertion marker 410 as illustrated in FIG. 4a on an outside surface of the sleeve 210 at a position selected to indicate that the distal end of the sleeve has been inserted to a predetermined distance into the distention valve and working channel of the hysteroscope. FIG. 4a illustrates an insertion marker 410 formed of two markings, a distal marking 401 and a proximal marking 402, on the outside of the sleeve 210. In an embodiment illustrated in FIG. 6a, the stabilization device 200 is inserted into the distention valve 610 of a hysteroscope 600 such that the distal marking 401 is inserted completely within the distention valve 610 and the working channel 620 of the hysteroscope 600 and the proximal marking 402 is outside of the distention valve 610 as illustrated in FIGS. 6b and 6c. In an embodiment, the proximal marking 402 is positioned so that the distal end of the stabilization device is inserted into the working channel to a depth sufficient to be clamped by the ball valve clamps 630 of the port valve switch 640. By inserting the stabilization device past the ball valve clamps 630 the possibility that the ball valve clamps may pinch or cut the delivery catheter of the intrafallopian contraceptive delivery device may be minimized. FIG. 6c illustrates a cut-away view of the inside of the distention valve 610 and the working channel 620 of the hysteroscope 600. Other embodiments of the insertion marker 410 are also contemplated by the invention, such as a single marking on the outside surface of the sleeve 210.

Figure 4B:
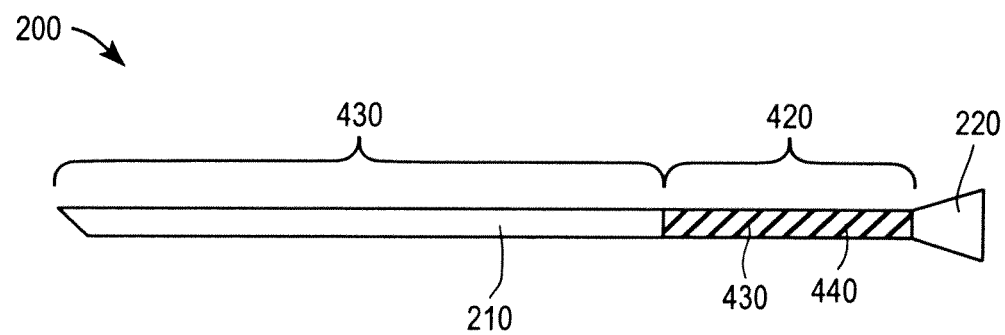
FIG. 4b is an illustration of a side view of a stabilization device formed of a sleeve having a flexible portion and an inflexible portion.
Figure 4C:
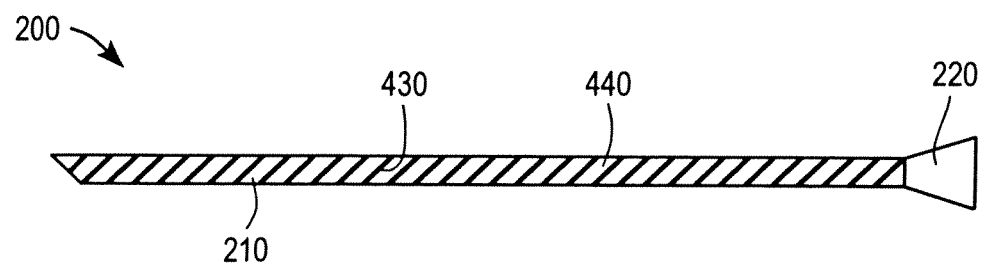
FIG. 4c is an illustration of a side view of a stabilization device formed of a flexible sleeve.
Figure 4D:
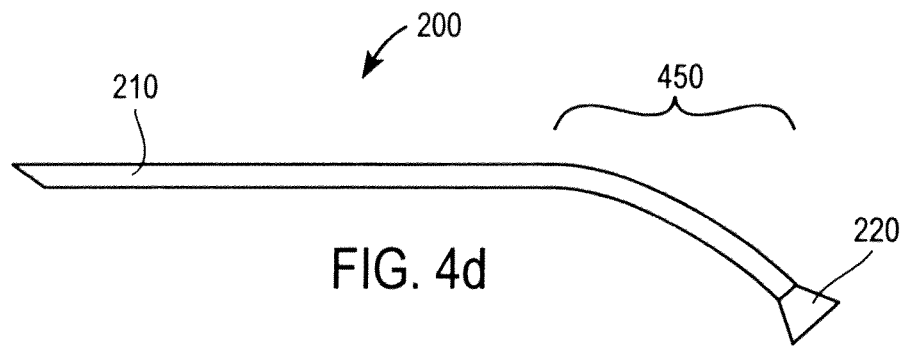
FIG. 4d is an illustration of a side view of a stabilization device formed of a sleeve curved on the proximal end.

FIG. 4b illustrates yet another embodiment of the stabilization device 200 where a portion 420 of the sleeve 210 is flexible and a portion 430 is inflexible. In some instances it may be beneficial for the stabilization device to have some flexibility to increase the maneuverability of the intrafallopian contraceptive delivery device to aid in the positioning of the insert within the fallopian tube. The flexibility of the sleeve 210 may also be valuable in enabling the operator of the delivery device to maneuver the handle around the hysteroscope if the angle of the working channel on the hysteroscope is close to the body of the hysteroscope. The flexible portion 420 of the sleeve 210 may be formed of a coil 430 coated with a polymer tubing material 440 that may also coat the inflexible portion 430. In an alternate embodiment, the entire sleeve 210 may be flexible. In one embodiment the flexible sleeve 210 illustrated in FIG. 4c may be formed of a coil 430 coated with a polymer tubing material 440.

Figure 4E:
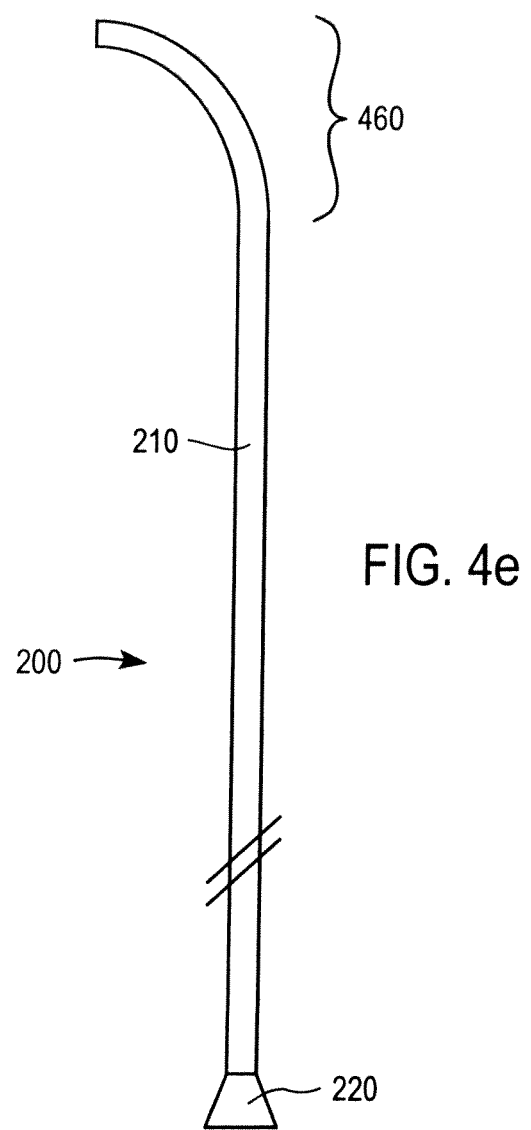
FIG. 4e is an illustration of a side view of a stabilization device formed of a sleeve curved on the distal end.
Figure 4:
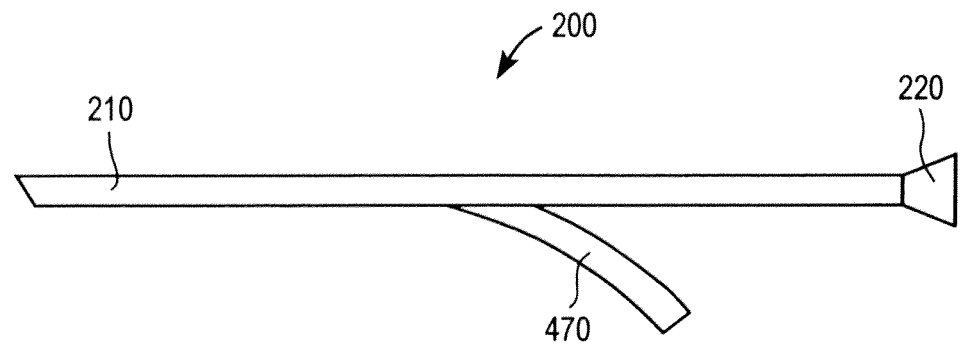
FIGS. 4f and 4g illustrate two embodiments of a stabilization devices which include at least one additional port.

In another embodiment the sleeve 210 of the stabilization sheath 200 may have a curved portion to increase the maneuverability of the device for the gynecological procedure. The sleeve 210 may have a proximal curved portion 450 as illustrated in FIG. 5d. Alternatively the sleeve 210 may have a distal curved portion 460 as illustrated in FIG. 4e. The distal curved portion 460 may facilitate the positioning of a fallopian tube insert from an intrafallopian contraceptive delivery device into a fallopian tube. In this embodiment the sleeve 210 may have a length sufficient to reach the fallopian tubes. The distal curved portion 460 may be formed of an inflexible material or it may be formed of a flexible material that may be bent at a desired angle by using adjustment wires (not illustrated) that would run the length of the sleeve 210 up to the distal curved portion.

Figure 4G:
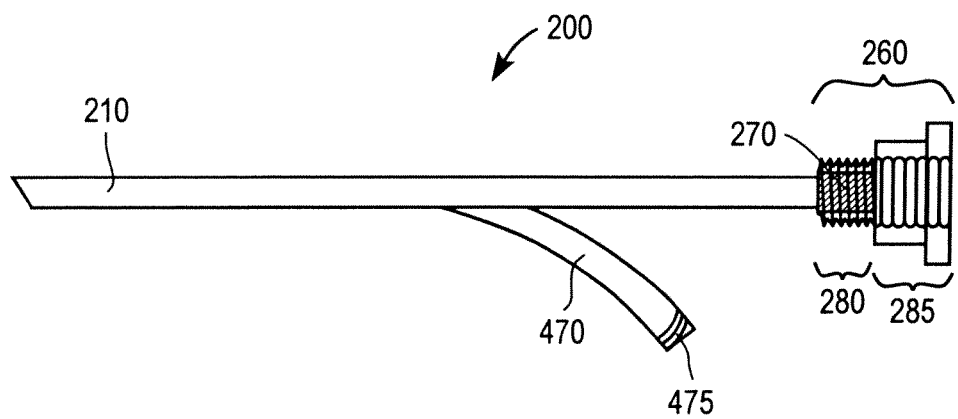

FIGS. 4f and 4g illustrate two embodiments of a stabilization device 200 having an additional port 470. The port 470 has a lumen continuous with the lumen of the sleeve 210. An additional delivery catheter may be inserted into a device that provides a transcervical pathway through the port 470, in addition to a delivery catheter that is coupled to a device for a gynecological procedure. In an embodiment, the port 470 may provide a pathway for an anesthetic delivery catheter or a contrast media delivery catheter. The port 470 may be straight or slightly curved and jutting from the sleeve 210 at any angle that is practical for the insertion of a catheter. In an embodiment illustrated in FIG. 4g the port 470 may have a screw thread 475 on the proximal end for the attachment of a screw-on device such as the tip of a syringe.

Figure 5A:
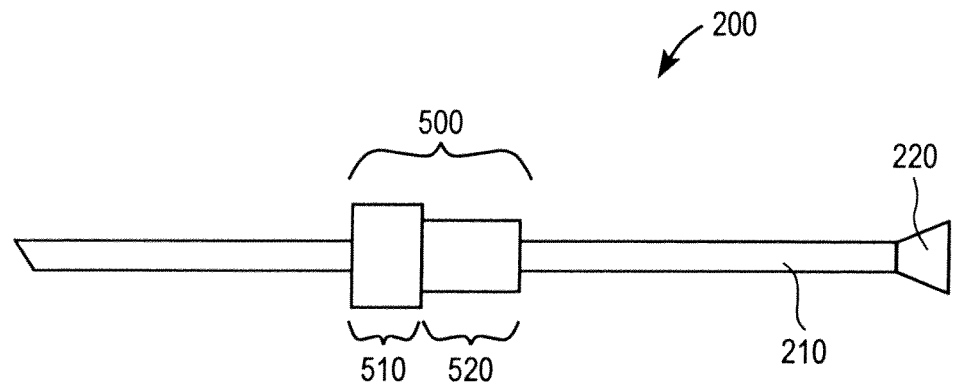
FIG. 5a is an illustration of a side view of a stabilization device having an embodiment of a distention valve for a hysteroscope attached to the sleeve.
Figure 5B:
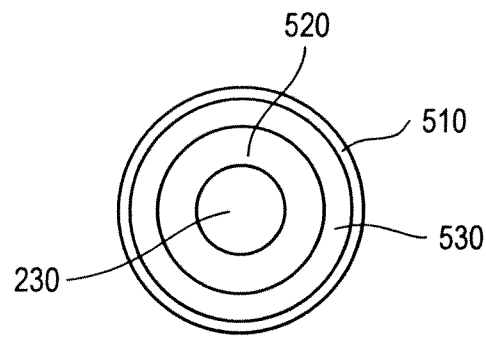
Figure 5C:
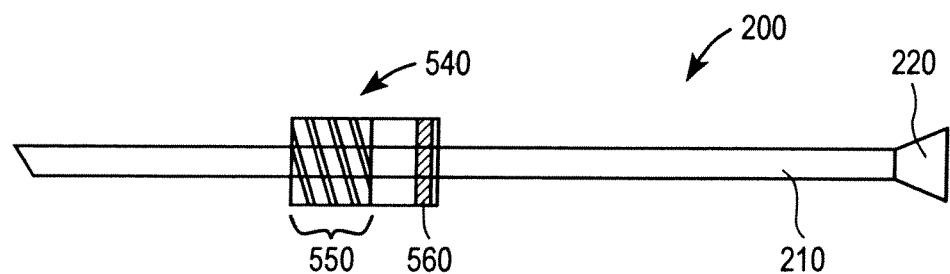
FIG. 5c is an illustration of a cross-sectional view of a stabilization device having another embodiment of a distention valve for a hysteroscope attached to the sleeve.
Figure 5D:
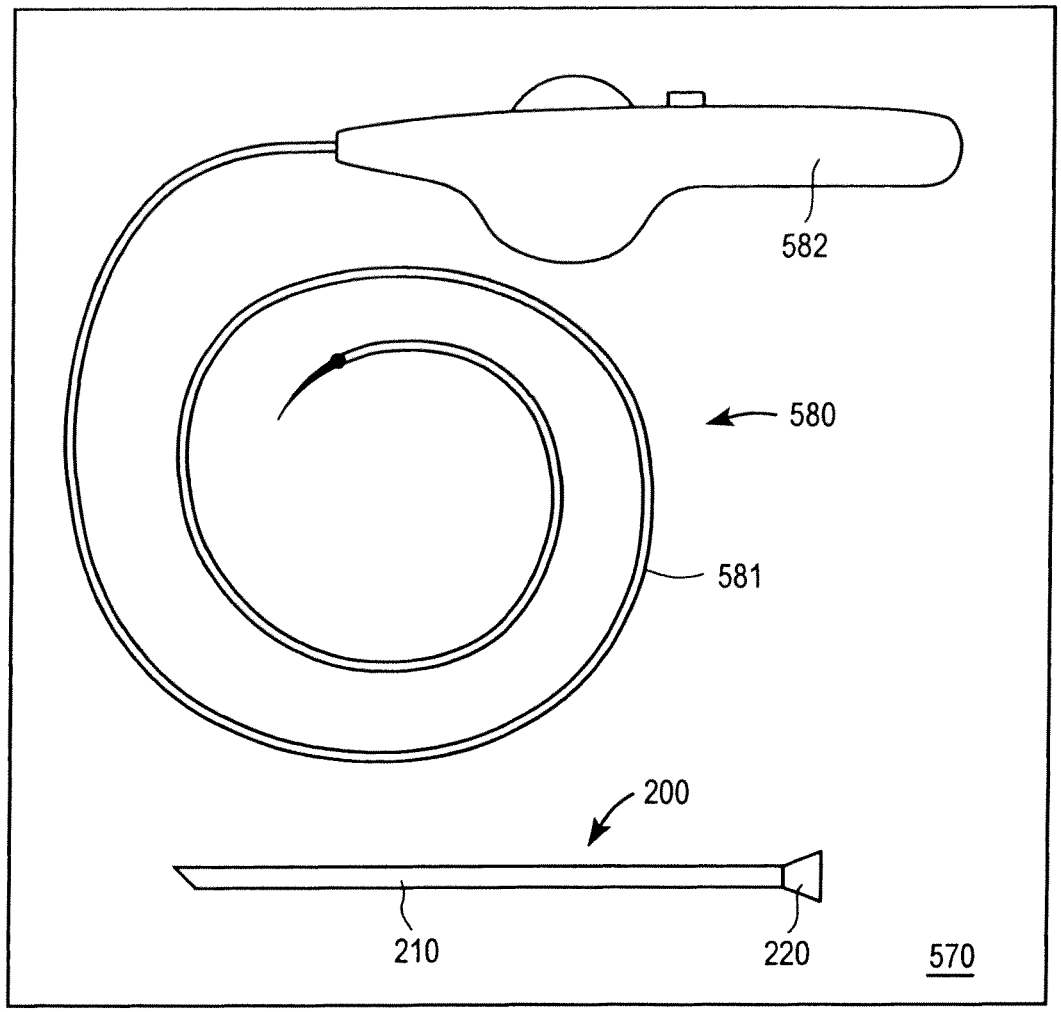
FIG. 5d illustrates a kit containing a stabilization device and an intrafallopian contraceptive delivery device.

FIG. 5a illustrates a stabilization device 200 that has a distention valve 500 coupled to the distal end of the sleeve 210. The distention valve may be formed of a soft rubber-like material that can form a seal around the working channel of a hysteroscope or another type of device that provides a transcervical pathway to prevent the backflow of fluid. In this exemplary embodiment the distention valve 500 is formed of a portion 510 that fits around a working channel of a hysteroscope. As illustrated in FIGS. 5a and 5b, the portion 520 of the distention valve 500 may have a smaller diameter than the portion 510 such that a shelf 530 is formed. The distention valve 500 couples to the sleeve 210 of the stabilization device 200 to form a continuous lumen between the distention valve 500 and the sleeve 210. In alternate embodiments the distention valve 500 may have a single diameter without the shelf 530. FIG. 5c illustrates an alternate embodiment of a distention valve 540 formed of a stiff material and containing an O-ring 560 to form a seal around the hysteroscope or another type of device that provides a transcervical pathway. The distention valve 540 may be formed of hard plastic and may have a screw-threaded portion 550 to be screwed on to a working channel of a hysteroscope or other device. The distention valves 500 and 540 illustrated in FIGS. 5a-5c may be fixed into place at any point on the sleeve 210 of the stabilization device 200 or may be movable along the sleeve 210 of the stabilization device 200.

FIG. 5d illustrates a kit 570 containing an intrafallopian contraceptive delivery device 580 and a stabilization device 200. The intrafallopian contraceptive delivery device may have a delivery catheter 581 and a control device 582 similar to the Essure device described above. The stabilization device 200 may have a sleeve 210 and a means for coupling the stabilization device to the control device 582 of the intrafallopian contraceptive delivery device. The stabilization device may alternately be any of the embodiments described above. The kit 570 may also include a hysteroscope such as the one illustrated in FIG. 6a. In another embodiment, the kit 570 may include a syringe loaded with a topical anesthetic. The syringe may have a first barrel and a second barrel, the first barrel loaded with the topical anesthetic and the second barrel loaded with a carrier. The topical anesthetic and the carrier may be mixed at the point of use with the use of a static mixer adapted to be coupled to the syringe. The static mixer may also be part of the kit 570.

In general, the current invention includes a method of coupling a stabilization device to a device that provides a transcervical pathway and coupling the stabilization device to a device for a minimally invasive gynecological procedure to stabilize the device for the minimally invasive gynecological procedure with respect to the device that provides the transcervical pathway. In one particular embodiment a control device of an intrafallopian contraceptive delivery device is stabilized with respect to a hysteroscope to fix the position of the fallopian tube insert within the fallopian tube. In this method, the delivery catheter of the intrafallopian contraceptive delivery device is inserted into a hysteroscope. The fallopian tube insert is then positioned within the fallopian tube for deployment. The position of the holding device with respect to the hysteroscope is then stabilized to fix the deployment position of the fallopian tube insert within the fallopian tube. The fallopian tube insert may then be deployed within the fallopian tube. The stabilization devices described above may be used to stabilize the position of the holding device with respect to the hysteroscope.

In an exemplary method of using the stabilization device 200, the stabilization device 200 is first coupled to the hysteroscope 600. The stabilization device 200 may be a sleeve 210 having a lumen and may be inserted into the working channel 620 of the hysteroscope 200 through a distention valve 610 that is attached to the end of the working channel 620 as illustrated in FIG. 6a. In this embodiment the distal end of the stabilization device 200 is inserted into the distention valve 610. The stabilization device 200 may be inserted into the distention valve 610 and the working channel 620 past a valve clamp 640. By inserting the sleeve 210 of the stabilization device 200 past the valve clamp 640 the valve clamp 640 may be used to couple the stabilization device 200 to the hysteroscope 200. Also, the sleeve 210 may be formed of a material that is hard enough not to be cut by the valve clamp 640 once it is clamped onto the sleeve 210. The valve clamp 640 may be a ball valve 630 as illustrated in FIG. 6c. Inserting the stabilization device 200 past the valve clamp 640 may also prevent the valve clamp 640 from snagging, pinching or cutting the delivery catheter and/or the guidewire of the intrafallopian contraceptive delivery device.

Markers may be placed on the outside of the sleeve 210 to indicate the depth to which the sleeve 210 should be inserted into the working channel 620. FIGS. 6a and 6b illustrate an embodiment where two markers 410, a distal marker 401 and a proximal marker 402, are on the outside of the sleeve 210. In this embodiment a first portion of the stabilization device 200 is inserted into the working channel 620 of the hysteroscope 600 until the distal marker 401 is entirely within the hysteroscope 600 and the proximal marker 402 is exposed immediately outside of the hysteroscope 600. In an alternate embodiment, there may be a single marker on the outside of the sleeve 210. In this embodiment, a first portion of the distal end of the sleeve 210 is inserted into the working channel 620 through the distention valve 610 until the marker is entirely within the hysteroscope 600, which in a particular embodiment may mean that the marker is entirely within the distention valve 610, and the proximal second portion of the stabilization device 200 remains outside of the hysteroscope 600.

In another embodiment, the stabilization device 200 may be coupled to a distention valve 500, such as those illustrated in FIGS. 5a-5c and in FIG. 6d. In this embodiment, the stabilization device may be coupled to the hysteroscope 600 by coupling the distention valve 500 to the proximal end of the working channel 620 of the hysteroscope 600. As illustrated in FIG. 6d, the distention valve 500 coupled the stabilization device 200 may be coupled to the hysteroscope 600 after inserting the distal end of the sleeve 210 of the stabilization device 200 into the working channel 620 of the hysteroscope. The distention valve 500 may be a rubber-like material that may fit onto the proximal end of the working channel 620 to form a seal. The distention valve 500 may also be screwed onto the proximal end of a working channel 620 having a screw thread (not illustrated.) The distention valve 500 in this embodiment may be fixed in place on the sleeve 210, in which case the depth at which the sleeve 210 is inserted into the hysteroscope 600 is determined by where the distention valve 500 is positioned on the sleeve 210. In another embodiment, the distention valve 500 is movable along the sleeve 210 and the depth at which the sleeve 210 is inserted into the hysteroscope 600 may be adjusted. In one particular embodiment, the sleeve 210 of the stabilization device 200 may have a length such that the sleeve 210 extends beyond the tip of the channel 670 of the hysteroscope 600. The insertion of the distal end of the sleeve 210 into the hysteroscope 600 in this embodiment may be facilitated by the coupling of the distention valve 500 to the sleeve 210. In this embodiment, the length of the sleeve 210 may be sufficient to reach the fallopian tubes of a patient. In this embodiment the distal end of the sleeve 210 may be slightly curved or bendable to guide a delivery catheter of an intrafallopian contraceptive delivery device towards the opening of a fallopian tube. The stabilization device 200 may be further coupled to the hysteroscope 600 by clamping the valve clamp 630 onto the sleeve 210, as illustrated in FIGS. 6b and 6c.

Figure 6F:
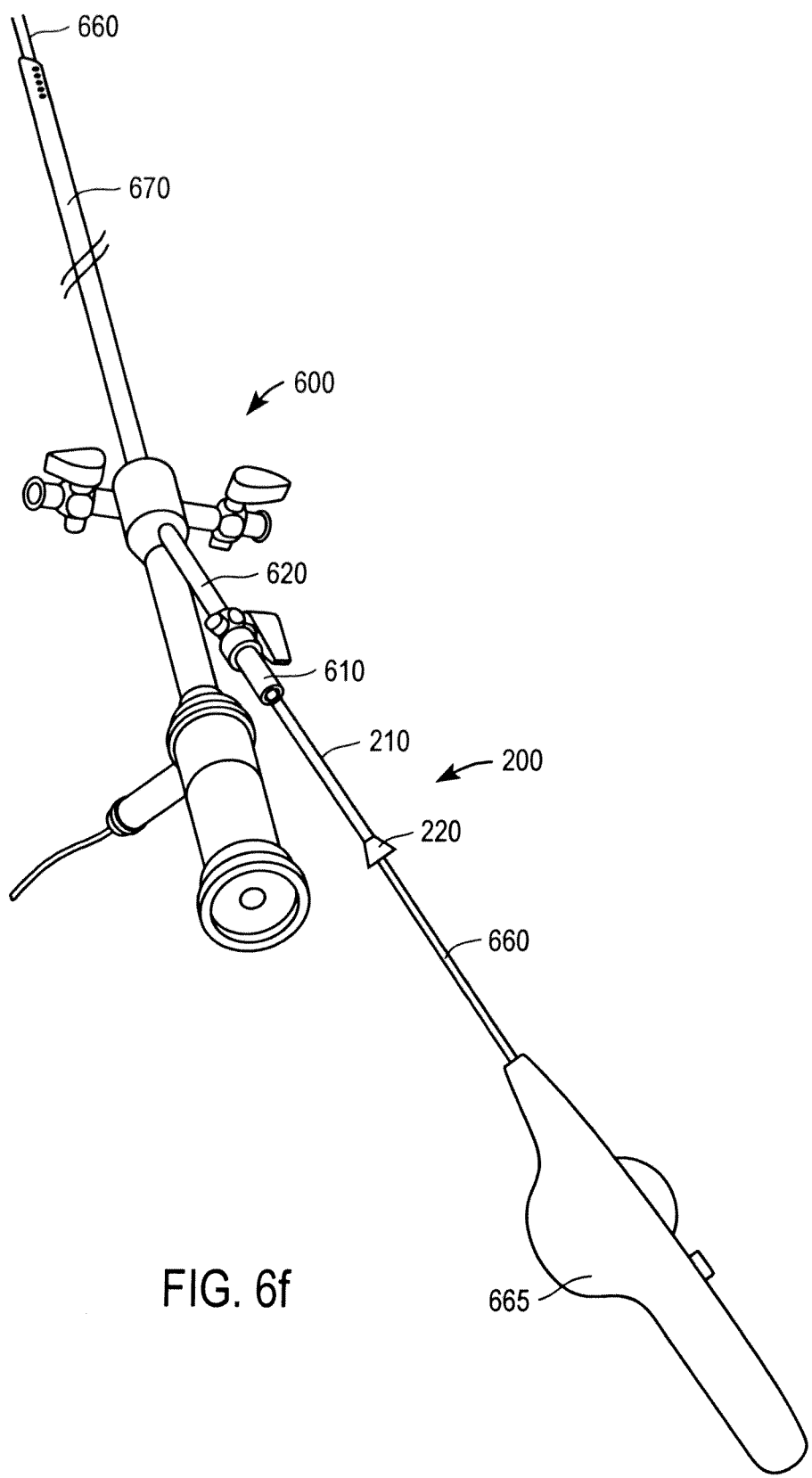
Figure 6:
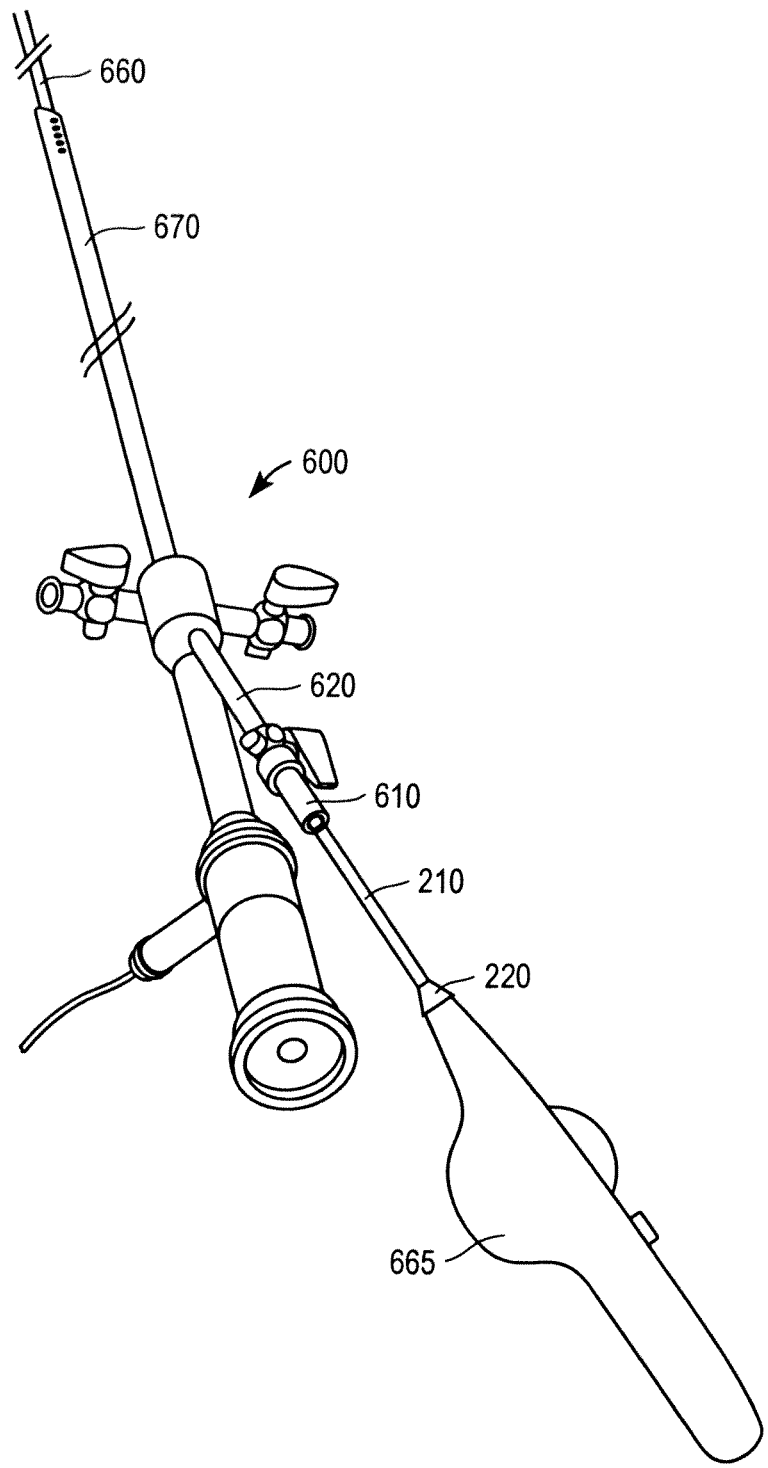
Figure 6:
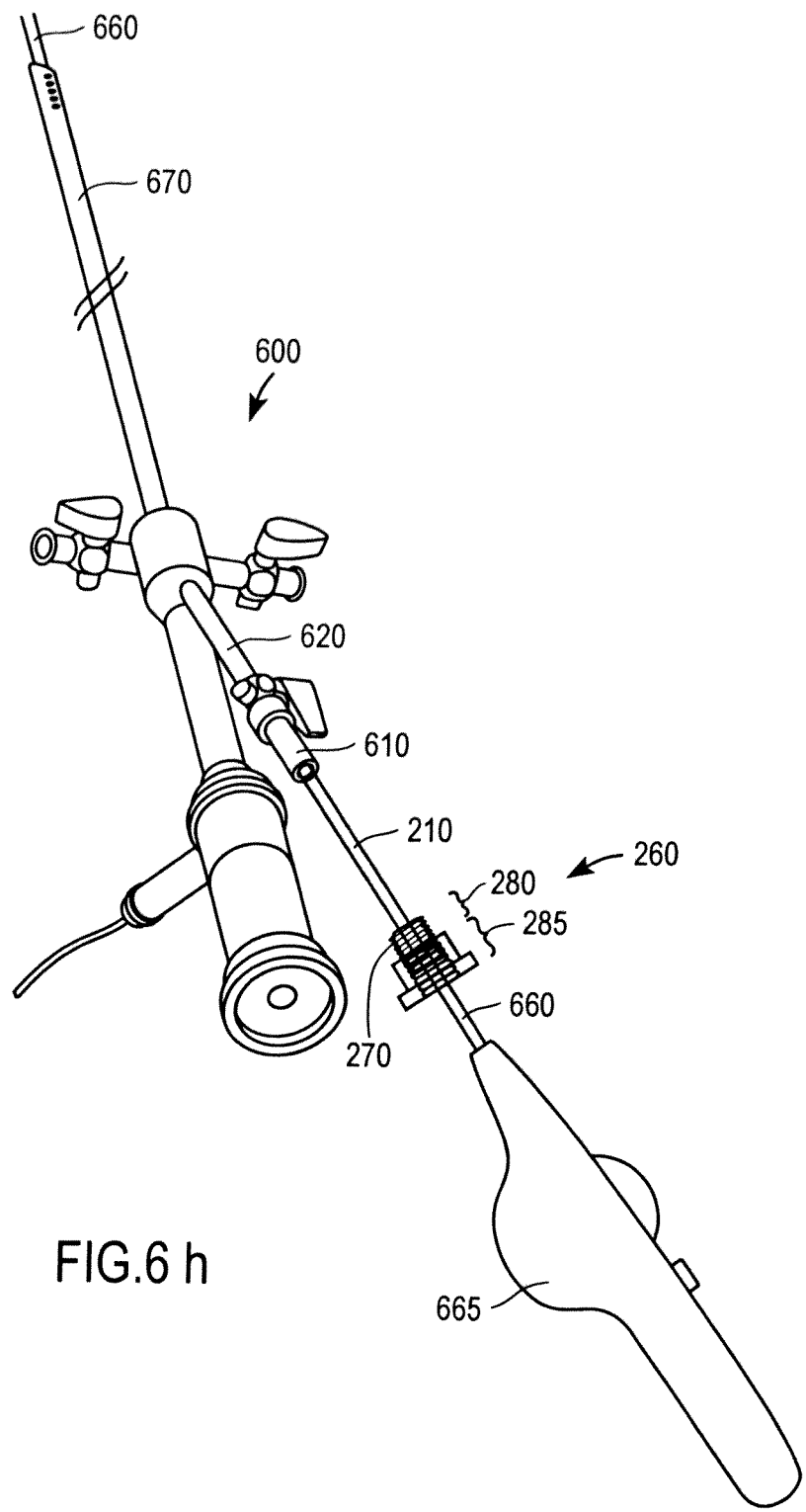

As illustrated in FIG. 6f, an intrafallopian contraceptive delivery device is inserted into the lumen of the stabilization device and the hysteroscope 600. The intrafallopian contraceptive delivery device may be formed of a delivery catheter 660 coupled to a holding device 665. In this embodiment, the delivery catheter 660 is inserted into the sleeve 210 of the stabilization device 200 and into the hysteroscope 600 through the working channel 610 and the channel 670. The delivery catheter 660 contains a fallopian tube insert for deployment into a fallopian tube. After passing through the channel 670 of the hysteroscope 600, the delivery catheter 660 passes through the uterus and into one of the fallopian tubes where the delivery catheter 660 is positioned for deployment of the fallopian tube insert. Once the delivery catheter 660 is positioned for deployment of the fallopian tube insert, the operator of the intrafallopian contraceptive delivery device may verify the position of the fallopian tube insert before coupling the stabilization device 200 to the control device 665.

The stabilization device 200 may then be coupled to the holding device 665. FIG. 6g illustrates an embodiment where the stabilization device 200 is coupled to the holding device 665 mechanically by a mechanical fitting 210 that snaps onto the holding device 665. In an alternate embodiment the stabilization device 200 may be coupled to the holding device 665 by a friction fitting, such as those illustrated in FIGS. 3a-3c.

In another embodiment, the stabilization device 200 may be coupled to the intrafallopian contraceptive device by coupling the stabilization device 200 to the delivery catheter 660. An example of this embodiment is illustrated in FIG. 6h. FIG. 6h illustrates a stabilization device 200 having an adjustable O-ring 260 at the proximal end. The inner diameter of the O-ring 270 may be tightened around the delivery catheter 660 by screwing the second sleeve 285 of the adjustable O-ring 260 onto the first sleeve 280 of the adjustable O-ring. The stabilization device 200 may also be coupled to the delivery catheter 660 by a simple O-ring having an inner diameter sufficient to form a seal around the delivery catheter 660. The adjustable O-ring 260 or a single O-ring may be formed in combination with a duckbill valve.

Figure 6I:
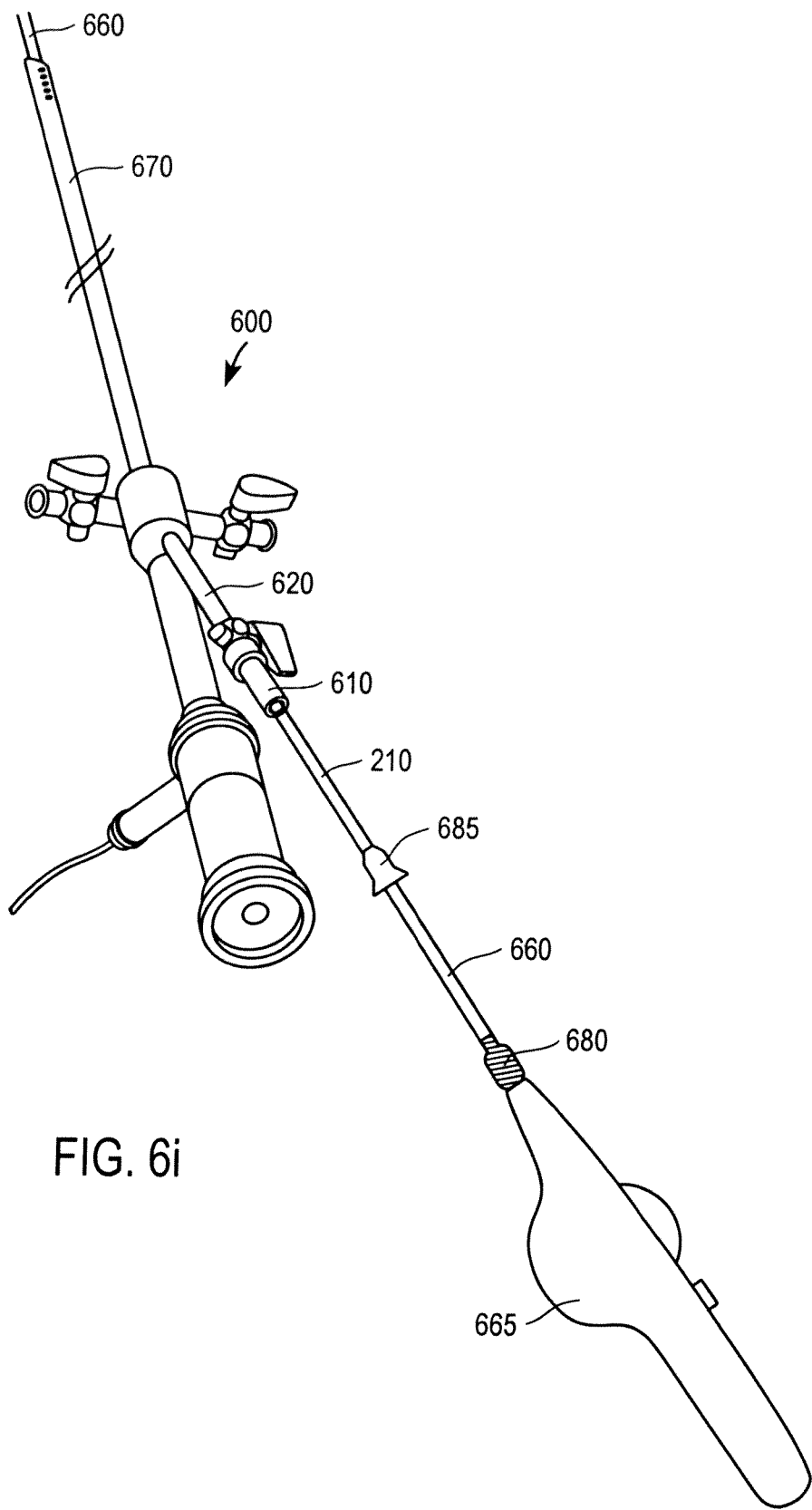
Figure 6J:
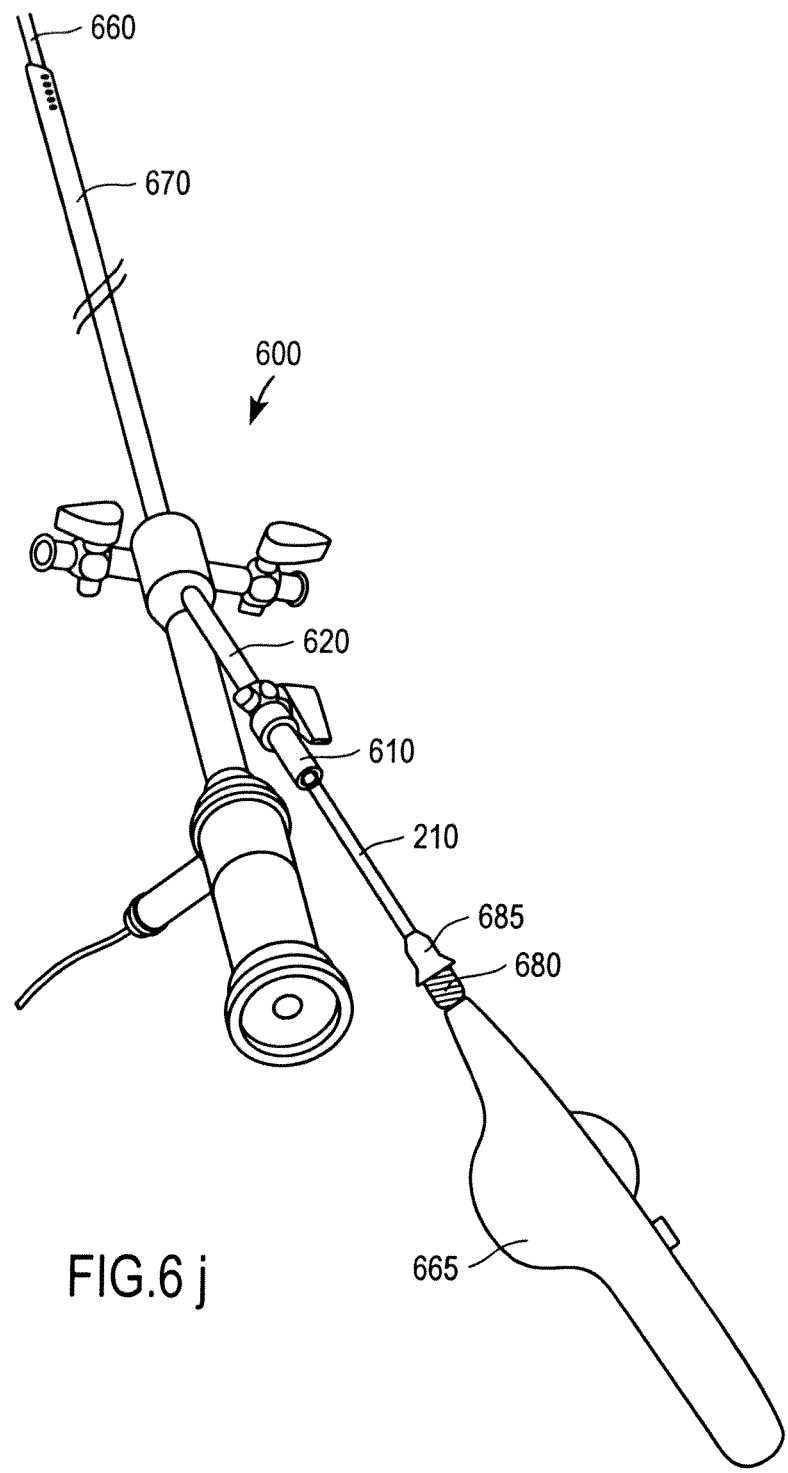

FIG. 6i illustrates another embodiment of a stabilization device 200 that may be coupled to the control device 665 of the intrafallopian contraceptive delivery device by a mechanical fitting. In this embodiment the mechanical fitting 685 is designed to mechanically fit onto an adaptor 680 that is coupled to the intrafallopian contraceptive delivery device. The adaptor 680 may be coupled to the control device 665 or to the delivery catheter 660. After positioning the intrafallopian contraceptive delivery device to deploy a fallopian tube insert the stabilization device 200 may be coupled to the intrafallopian contraceptive delivery device by mechanically fitting the mechanical fitting 685 to the adaptor 680.

In yet another embodiment, the stabilization device 200 may be pre-coupled to the intrafallopian contraceptive delivery device. In this embodiment it would not be necessary to couple the stabilization device 200 to the intrafallopian contraceptive delivery device.

The position of the fallopian tube insert for deployment from the delivery catheter 660 may be verified and adjusted again before coupling or re-coupling the stabilization device 200 to the hysteroscope 600. In one embodiment, the verification and potential adjustment of the position of the fallopian tube insert for deployment may be performed prior to clamping the valve clamp 630 onto the sleeve 210 of the stabilization device 200. In one embodiment, the positioning of the fallopian tube insert for deployment may be adjusted after coupling the stabilization device to the intrafallopian contraceptive delivery device by using a feed-forward mechanism of the intrafallopian contraceptive delivery device. FIGS. 6k-6m illustrate this embodiment with a cut-away side view of the control device 665 of an intrafallopian contraceptive delivery device. In FIG. 6k the distal tip of the intrafallopian contraceptive delivery device is at a first position beyond the ostium 675 within a fallopian tube and the stabilization sheath 200 is coupled to the adapter 680 by the mechanical fitting 685. In FIG. 6l, a user of the control device 665 may then roll back the thumbwheel 667 of the control device 665 to mechanically fit the adapter 680 to the control device mechanical fitting 687 and to feed-forward the core wire 671.

In an embodiment, the core wire 671 is moved forward into the fallopian tube by approximately 1.6 cm to compensate for user error. In FIG. 6m, rolling back the thumbwheel 667 will break away a portion 672 of the sheath 673 that contains the delivery catheter 660. After the portion 672 of the sheath 673 breaks away inside of the control device 665, the delivery catheter 660 is retracted to uncover the core wire 671 to expose the fallopian tube insert (not shown) that is wound down over the core wire 671.

The position of the delivery catheter 660 for the deployment of the fallopian tube insert may be verified by fluoroscopy, ultrasound (including hysterosalpingo-contrast-ultrasonography (HyCoSy) and stimulated acoustic emission (SAE-HyCoSy)), radiography, or visual orientation using a camera placed through the hysteroscope 600. In one embodiment the distal end of the delivery catheter 660 or the distal end of a stabilization device 200 having a length sufficient to reach the fallopian tubes may be marked with a radiopaque material that may be viewed by radiography. In this embodiment the positioning and verification of the position of the delivery catheter 660 for the deployment of the fallopian tube insert may be done by viewing the radiopaque mark on either the delivery catheter 20 or on the distal end of the stabilization device 200.

Alternatively, the uterus may be distended using a contrast media that is visible by either ultrasound or radiography for the positioning and verification of the position of the delivery catheter 660 for the deployment of the fallopian tube insert. In one embodiment, the contrast media may be a fluid or gel containing microbubbles that are a shell filled with a contrast agent such as a gas or other ultrasound contrast enhancing agent viewable by ultrasound such as perfluorocarbon-exposed sonicated dextrose albumin microbubbles. In an embodiment, the microbubbles may contain a topical anesthetic such as lidocaine that may be delivered to the uterine cavity by applying ultrasound at an energy sufficient to cause the microbubbles to burst and release the anesthetic. In one exemplary method, the positioning of the stabilization sheath 200 or the delivery catheter 600 may be accomplished using ultrasound to view the contrast media within the microbubbles. The microbubbles may then be burst by changing the ultrasound energy to release the anesthetic into the uterine cavity. The release of the anesthetic from the microbubbles may be monitored and regulated by measuring the harmonic response to the ultrasound energy. In another embodiment the anesthetic may be released from some of the microbubbles prior to the performance of the minimally invasive gynecological procedure to an extent that would anesthetize the tissues surrounding the uterine cavity but to still have microbubbles remaining for ultrasound positioning of the device for the minimally invasive gynecological procedure.

FIGS. 7a-7d illustrate an alternate embodiment where the device that provides the transcervical pathway is an access catheter. In this embodiment the access catheter has a balloon to form a seal between the access catheter and the cervix and to fix the position of the access catheter during a minimally invasive gynecological procedure. FIG. 7a illustrates a cut-away side view of the access catheter 700 having a tubular catheter body 710 that includes a distal end 712 and a proximal end 714 and a lumen 715. The lumen 715 provides a transcervical pathway to access the uterine cavity with a surgical instrument. An elongated inflatable balloon 720 (illustrated in the deflated state) is sealingly affixed to and encloses a distal portion of the catheter body 710. The balloon 720 contains a fixed residual volume of fluid which is displaced by operation of the fluid displacement sleeve 730. FIG.

7b illustrates the outer surface of the access catheter 700. FIG. 7c illustrates the balloon 720 of the access catheter 700 once it is placed within the os of the cervix.

The displacement sleeve 730 may then be slid along the outside of the catheter 710 towards the distal end 712 of the tubular catheter body 710 to displace the fixed residual volume of fluid into the portion of the balloon 720 that is within the os of the cervix. FIG. 7d illustrates the expanded balloon 720 in the cervix region after the displacement sleeve 730 has been slid towards the distal end 712 of the tubular catheter body 710. The expanded balloon 720 serves to hold the access catheter 700 in place during a minimally invasive gynecological procedure such as the use of an intrafallopian contraceptive delivery device to place fallopian tube inserts within the fallopian tubes.

Similar to the use of the stabilization sheath 200 with the hysteroscope 600, the stabilization sheath 200 may be coupled to the end of the access catheter 700 to provide a pathway for a device for a nonsurgical gynecological procedure and to provide a means for coupling the stabilization device to the device for the nonsurgical gynecological procedure. The stabilization device 200 may be coupled to the access catheter 700 by a distention valve 500 that has formed a seal by friction fitting with the tubular catheter body 710. The stabilization device 200 may be coupled to the tubular catheter body 710 by other means such as an O-ring, and adjustable O-ring, or a screw thread. The stabilization device 200 also has a means for coupling the stabilization device 200 to the device for a minimally invasive gynecological procedure such as a mechanical fitting 220 or any of the other embodiments described above in relation to the hysteroscope embodiment. The stabilization device 200 may also have a port 470. Any of the methods described above in relation to the hysteroscope embodiment may be applied to the use of the access catheter 700 in place of the hysteroscope. The stabilization device 200 may be valuable for use with the access catheter because it provides a stable fixed longitudinal distance between the device for the minimally invasive gynecological procedure and the access catheter during the gynecological procedure. This may significantly improve the accuracy of the gynecological procedure. For example, the accuracy of placement of fallopian tube inserts from an intrafallopian contraceptive delivery device may be improved.

Figure 8A:
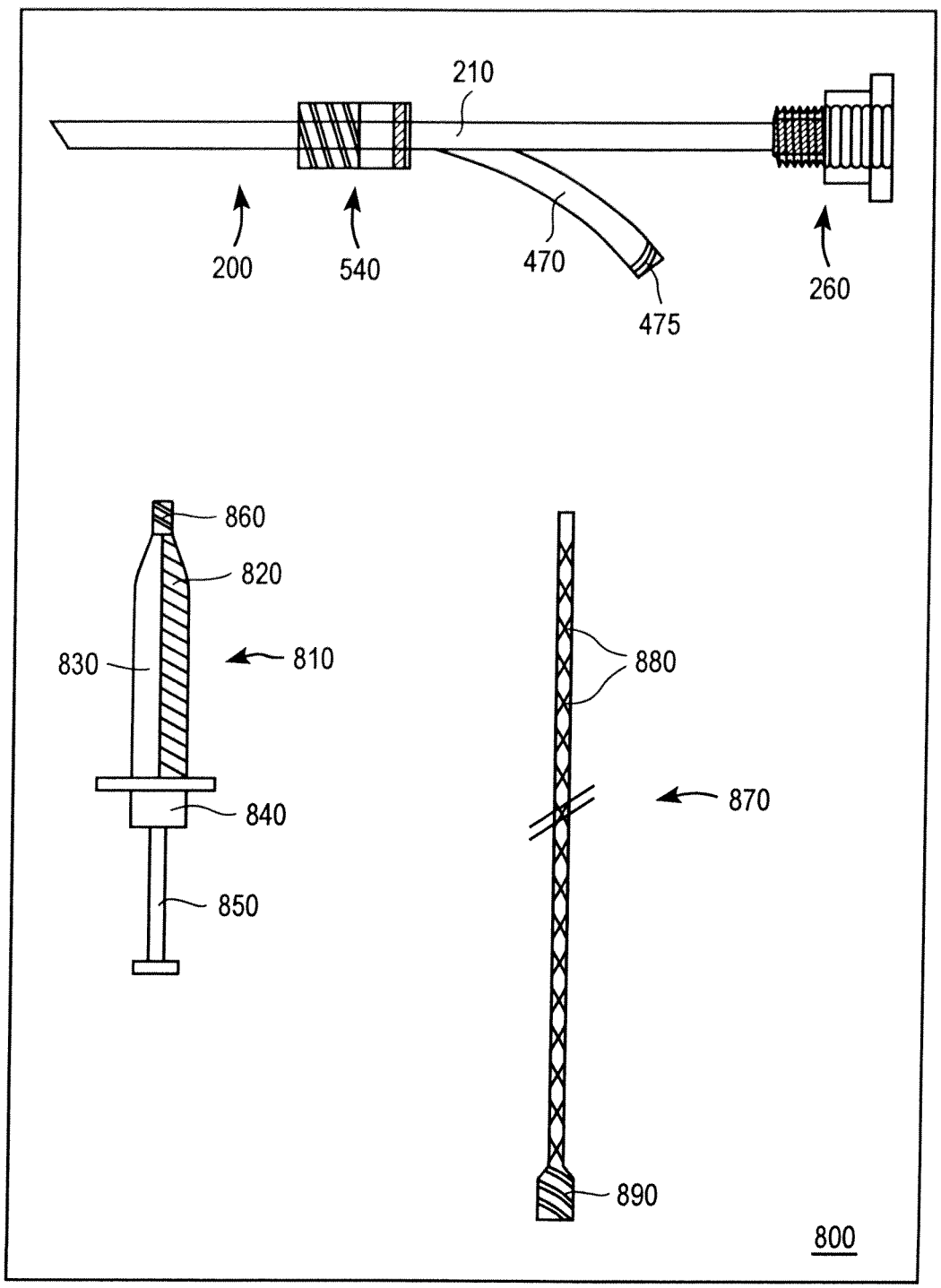
FIG. 8a illustrates a kit containing a stabilization device having a port for an anesthetic delivery catheter, an anesthetic delivery catheter that has static mixer capabilities, and a dual-barrel syringe.

In another embodiment, prior to a minimally invasive gynecological procedure, a topical anesthetic may be applied to the uterus. In a method of a minimally invasive procedure of placing fallopian tube inserts into the fallopian tubes the topical anesthetic may be applied to a region around the opening of the fallopian tubes (the ostium). The topical anesthetic may be delivered to the uterus using a port on a stabilization device. FIG. 8a illustrates a kit 800 containing a stabilization device 200 having a port 470, a syringe 810, and an anesthetic delivery catheter 870. The stabilization device 200 having a port 470 may be in the form of any of the embodiments discussed above. In the embodiment illustrated in FIG. 8a the stabilization device 200 is formed of a sleeve 210 to which a distention valve such as 540 may be coupled and to which an adjustable O-ring 260 may be coupled. The port 475 may also include a screw thread at the proximal end to screw the syringe 810 to the port 470. The syringe 810 may be a single-barreled syringe or a dual-barreled syringe as illustrated in FIG. 8a. A single-barreled syringe may be pre-loaded with an anesthetic mixture or may be filled by a physician performing a gynecological procedure.

The anesthetic mixture may by an anesthetic such as lidocaine hydrochloride and may have a concentration in the range of 0.5% and 15%, and more particularly in the range of 5% and 10%. In an alternate embodiment, the topical anesthetic may be a mixture of an amide anesthetic such as lidocaine, lignocaine, marcaine, or carbocaine, a buffering agent to bring the pH of the mixture to at least 5.5, optionally a viscosity agent and/or a solubilising agent. In an embodiment, the viscosity agent is present in an amount sufficient to give the topical anesthetic a viscosity greater than water and to maintain viscosity at body temperature. In one particular embodiment, the viscosity agent may be hydroxypropyl methylcellulose. The solubilizing agent serves to inhibit crystallization and therefore also the precipitation of the anesthetic compounds within the topical anesthetic mixture. An example of a solubilizing agent that may be used in the formulation is N-methyl-2-pyrrolidone. The solubilizing agent enables the solution to hold a higher concentration of the anesthetic agent and thereby increases the bio-availability, potency, and effect of the anesthetic agent. Additionally, the topical anesthetic may contain materials that enhance the absorption of the anesthetic into a patient's tissues.

The topical anesthetic may be mixed at a point of use to further prevent the precipitation of the anesthetic agent before application and to prolong the shelf-life of the anesthetic agent. The potency of the topical anesthetic may decrease once the anesthetic agent is mixed with a carrier material, therefore point of use mixing ensures that the topical anesthetic applied to the uterus and the fallopian tubes is potent.

A dual-barreled syringe 810 may be used to mix the topical anesthetic at the point of use. The dual-barreled syringe has a first barrel 820 to contain a topical anesthetic such as lidocaine hydrochloride. The topical anesthetic within the first barrel 820 may have a concentration in the range of 2% and 15% anesthetic, and more particularly may have a concentration of approximately 12%. The topical anesthetic may be a liquid, a paste, or a gel. The second barrel 830 may contain a carrier material that will be mixed with the topical anesthetic from the first barrel 820. In an embodiment, the carrier material may be a buffer agent or a buffer agent in combination with a solubilizing agent and a viscosity agent. The topical anesthetic may further contain materials that prolong the shelf-life of the anesthetic if the syringe is pre-loaded.

The syringe 810 also has a plunger 850 and a tip 860 that may have a screw thread for attachment to the anesthetic delivery catheter 890 or the port 470. The syringe 810 may also include a lock 840 to prevent the leakage of the contents of the syringe if pre-loaded.

The kit 800 may also include an anesthetic delivery catheter 870. The anesthetic delivery catheter 870 may have a length sufficient to apply the topical anesthetic mixture to any portion of a uterus or a cervix. In an embodiment, the length of the anesthetic delivery catheter is a length sufficient to apply the topical anesthetic mixture to the region in the uterus around the fallopian tubes. The anesthetic delivery catheter 870 may also have static mixing portions 880 to mix the contents of a dual barrel syringe at the point of use as the topical anesthetic and the carrier are mixed. The static mixer portions 880 may extend the entire length of the anesthetic delivery catheter 870 or may extend for only the length necessary to sufficiently mix the topical anesthetic with the carrier. The anesthetic delivery catheter 870 may also be an ordinary catheter without static mixing capabilities. The anesthetic delivery catheter 890 may have a screw thread at the proximal end for coupling with the syringe 810 or with the proximal end of the port 470 after insertion of the anesthetic delivery catheter into the port 470. A biocompatible polymer may be used to form the anesthetic delivery catheter 870 and may be flexible. The anesthetic delivery catheter 870 may be reusable or disposable.

The kit 800 may also include a static mixing tip (not illustrated). The proximal end of the static mixing tip may be coupled to the tip 860 of the syringe 810. The length of the static mixing tip depends on the amount of mixing necessary to sufficiently mix a topical anesthetic with a carrier. The distal end of the static mixing tip may be coupled to and anesthetic delivery catheter 870 and/or to the port 470.

Figure 8B:
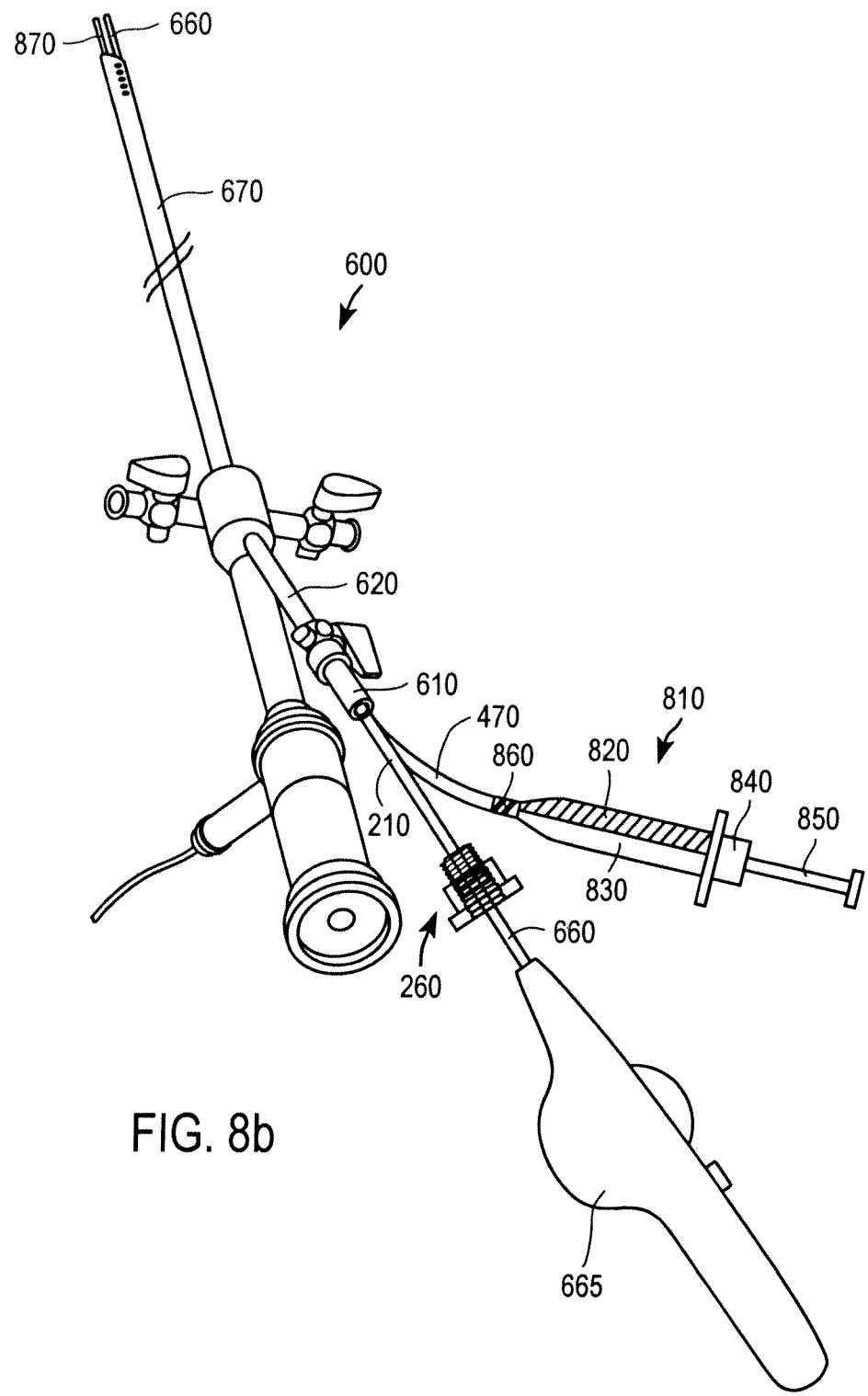
FIG. 8b illustrates a stabilization device having a port for an anesthetic delivery catheter coupled to a syringe containing an anesthetic and anesthetic carrier.

FIG. 8*b* illustrates the use of the components of the kit 800 with a hysteroscope 600. The components of the kit 800 and the different embodiments of the components of the kit 800 may also be used with an access catheter 700 such as the one illustrated in FIGS. 7*a*-7*d*. A stabilization device 200 having a port 470 into which the anesthetic delivery catheter has been inserted and to which a syringe 810 has been coupled is illustrated. The topical anesthetic may be applied to the uterus or cervix before inserting the delivery catheter 660 for the intrafallopian contraceptive device into the stabilization device 200 and the hysteroscope 600.

In an embodiment, the topical anesthetic may be a mixed with a carrier at the point of use using a static mixer within the anesthetic delivery catheter 870 once the topical anesthetic in the first barrel 820 and the carrier in the second barrel 830 of the dual barrel syringe 810 are injected into the anesthetic delivery catheter 870 by unlocking the lock 840 and depressing the plunger 850. The syringe 810 may have been preloaded or may be loaded at the point of use. The anesthetic delivery catheter may be positioned to deliver the topical anesthetic to a particular region of the uterus or cervix by ultrasound or radiography, as well as by visual orientation using a camera in a hysteroscope. To position the anesthetic delivery catheter by radiography, the tip of the anesthetic delivery catheter may have a radiographic marker at the distal end. Alternatively, the uterus may be distended with a contrast media for ultrasound or radiography prior to the application of the topical anesthetic. The minimally-invasive gynecological procedure may be performed between 2 minutes to 24 hours after the application of the topical anesthetic. The topical anesthetic may need a few minutes to take effect. In one particular embodiment, the minimally-invasive gynecological procedure may be performed within the approximate range of 5 minutes and 20 minutes after the application of the topical anesthetic.

Once the delivery catheter of the intrafallopian contraceptive delivery device is positioned to deploy the fallopian tube insert the fallopian tube insert is deployed into the fallopian tube. In an embodiment, the fallopian tube insert may have the general structure of a metal frame formed from a metal such as stainless steel or superelastic or shape memory material. The frame may be expanded radially from a first diameter to a second diameter that is larger than the first diameter. The insert may expand in a way that causes it to resiliently apply an anchoring force against the wall of the fallopian tube. The surface of the insert may be designed to facilitate epithelial growth; one way of doing this is to provide the insert with and open or lattice-like framework to promote and support epithelial growth into as well as around the insert to ensure secure attachment to an embodiment within the wall of the body lumen. The hollow inner portion within the frame may include a tissue ingrowth agent such as a polyester fiber or other materials known to facilitate fibrotic or epithelial growth. The surface of the frame may also be modified or treated or include such a tissue ingrowth material.

In other embodiments, the device may be coated or seeded to spur epithelialization. For example, the device can be coated with a polymer having impregnated therein a drug, enzyme or protein for inducing or promoting epithelial tissue growth. Once a fallopian tube insert has been placed into one fallopian tube the methods described above may be repeated to place a fallopian tube insert into the second fallopian tube. This may be done with the same delivery catheter 660 if the delivery catheter 660 contains two fallopian tube inserts in series or in parallel within a delivery catheter that has two lumens. Alternatively the second fallopian tube insert may be inserted with a second intrafallopian contraceptive delivery device.

Figure 9:
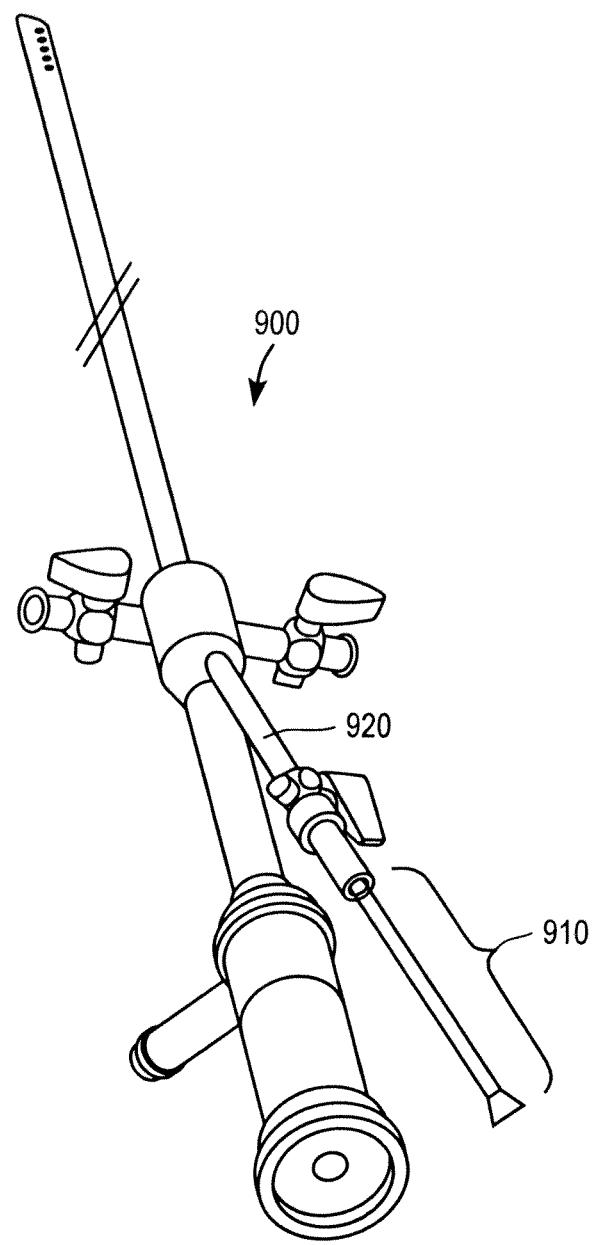
FIG. 9 illustrates a stabilization device permanently coupled to a hysteroscope.

In an alternate embodiment, illustrated in FIG. 9, the stabilization device 910 may be permanently coupled to a hysteroscope 900. The stabilization device 910 may be coupled to the working channel 920 as an integrated part.

Figure 10:
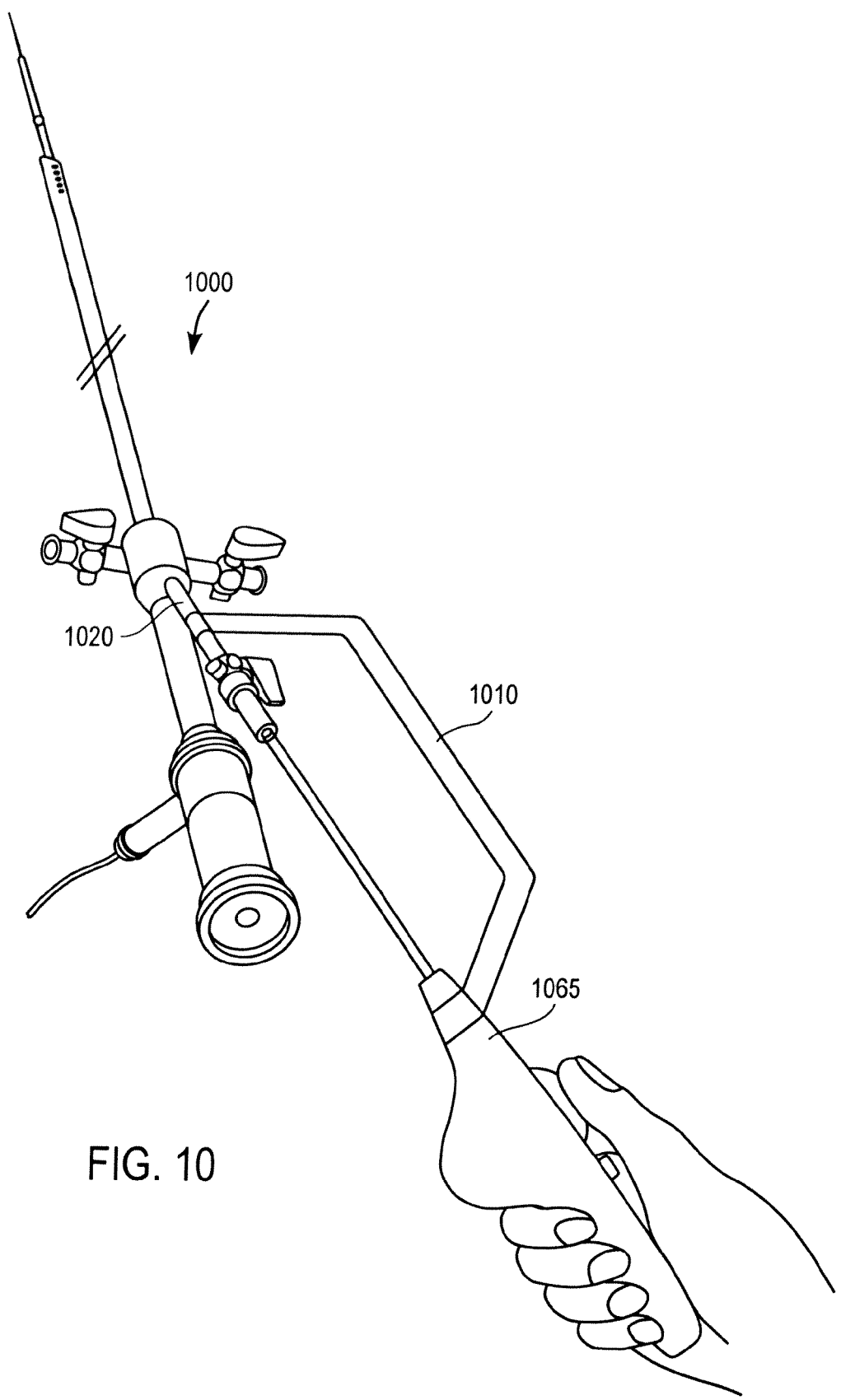
FIG. 10 illustrates an embodiment of a stabilization device shaped like an arm.

In another embodiment, the stabilization device may be an arm. FIG. 10 illustrates one example of this embodiment where the stabilization device is an arm 1010 that is coupled to the hysteroscope 1000 and the handle of the control device 1065 to create a fixed distance between the hysteroscope 1000 and the control device 1065. In this particular embodiment, the stabilization device shaped like an arm is coupled to the working channel 1020 and to the front portion of the handle of the control device 1065. The stabilization device 1010 shaped like an arm may be coupled to the hysteroscope 1000 and to the control device 1065 at other various points sufficient to fix the position of the hysteroscope 1000 with respect to the control device 1065.

Figure 11A:
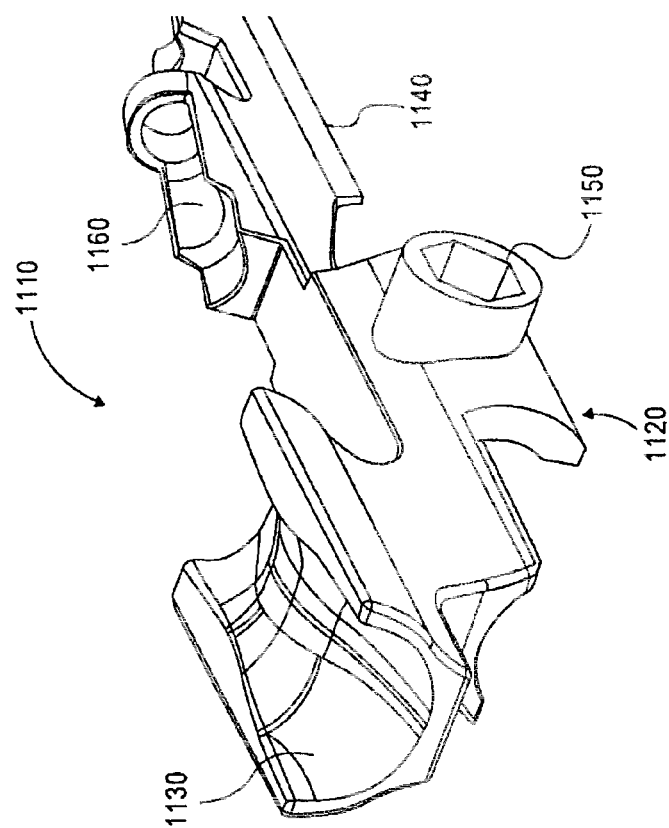
FIG. 11a is an isometric view of a stabilization arm.

FIG. 11*a* shows a stabilization arm 1110. The arm has an elongated body with a first fitting 1120 for coupling to a endoscope and a contoured holster 1130 for mounting a medical device. A second optional fitting 1140 for coupling to the endoscope is also shown. A mounting point 1150 for an optional handle 1160 is also shown. The handle 1160 may be shaped to be grasped by an operator's hand. The mounting point 1150 may also be used for other attachments, such as a table clamp or pole mount. The stabilization arm 1110 may be made out of a flexible polymer allowing the first fitting 1120 and second fitting 1140 to "snap" onto the endoscope. Alternatively the stabilization arm 1110 may be made out of a harder plastic or metal allowing the stabilization arm 1110 to slide onto an endoscope. The use of the stabilization arm 1110 is advantageous because it allows an operator to perform a medical procedure without a second assistant to manipulate the medical device or endoscope. The stabilization arm 1110 also helps to prevent a too distal placement of a medical implant, such as a fallopian tube contraceptive implant device. The handle 1160 may be locked in a position relative to the hysteroscope or other type of endoscope by the stabilization arm 1110, and this position prevents a deployment of the implant in a too distal position (or too proximal location or both). Hence, in addition to making it easier to control and use the delivery catheters which is controlled by the handle 1160, the stabilization arm 1110 improves the accuracy of placement of the implant which is deployed by the delivery catheter.

Figure 11B:
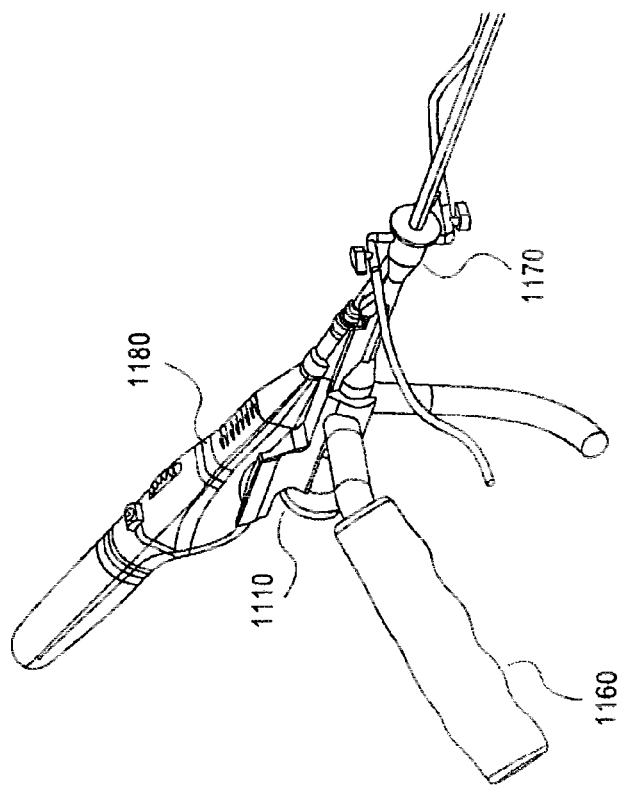
FIG. 11b is an isometric view of the stabilization arm of FIG. 11a mounted to an endoscope and holstering a medical device such as a control device for performing a transcervical medical procedure.

FIG. 11*b* shows the stabilization arm 1110 mounted to an endoscope 1170. The medical device 1180 is shown holstered securely into the stabilization arm 1110. The optional handle 1160 is installed. The optional handle 1160 allows the operator to use the endoscope 1170 while grasping onto the handle 1160 as the primary point of manipulation. The medical device 1180 may be a proximal control handle for deploying a fallopian tube contraceptive implant, such as a control device 665 or similar devices.

Figures 12A, 12B:
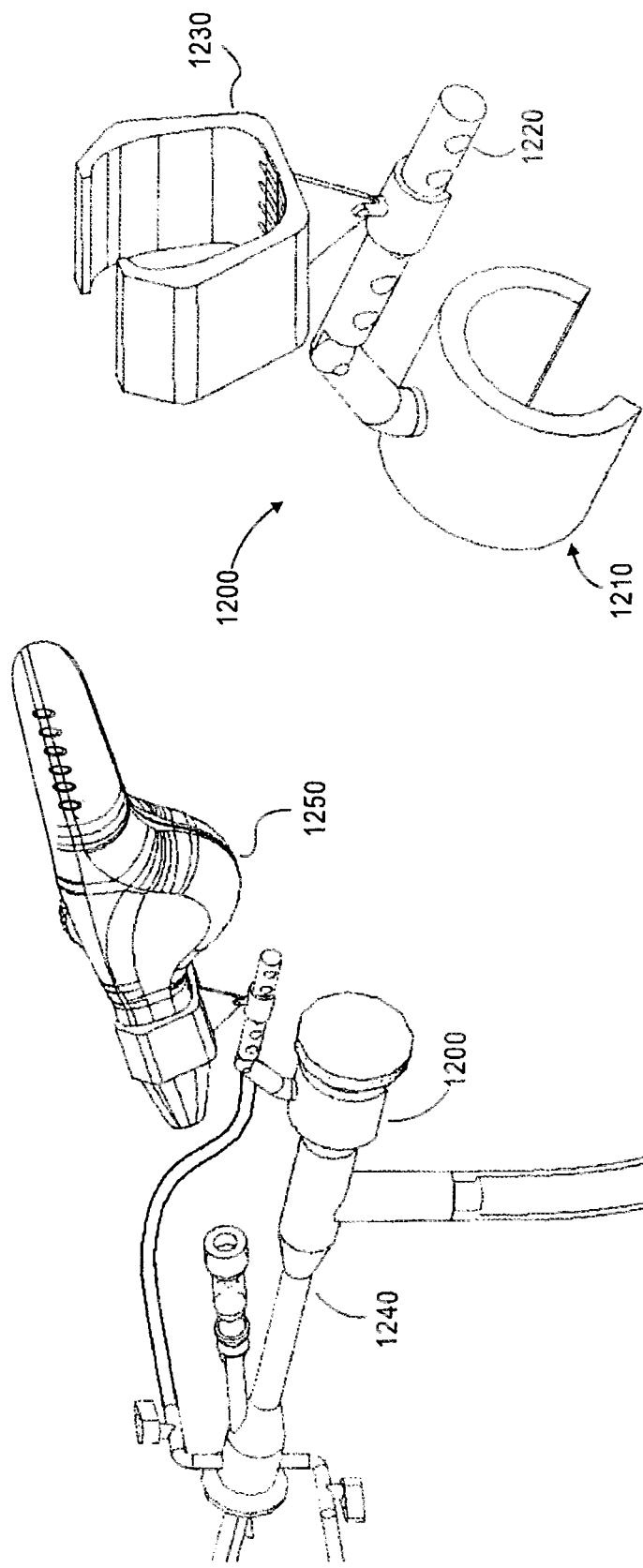
FIG. 12a is an isometric view of a stabilization arm.
FIG. 12b is an isometric view of the stabilization arm of FIG. 12a mounted to an endoscope and holstering a medical device such as a control device for performing a transcervical medical procedure.

FIG. 12*a* shows a stabilization arm 1200. The stabilization arm 1200 includes a circular clamp 1210 for mounting onto an endoscope. An optional extension member 1220 extends from the clamp 1210. The clamp 1210 includes an elongated member rotatably hinged to the clamp 1210. A holster 1230 for mounting a medical device slides and rotatably hinges on the clamp allowing maximum adjustment capability.

FIG. 12*b* shows the stabilization arm 1200 mounted onto an endoscope 1240. A medical device 1250 is shown holstered into the stabilization arm 1200.

Figure 13A:
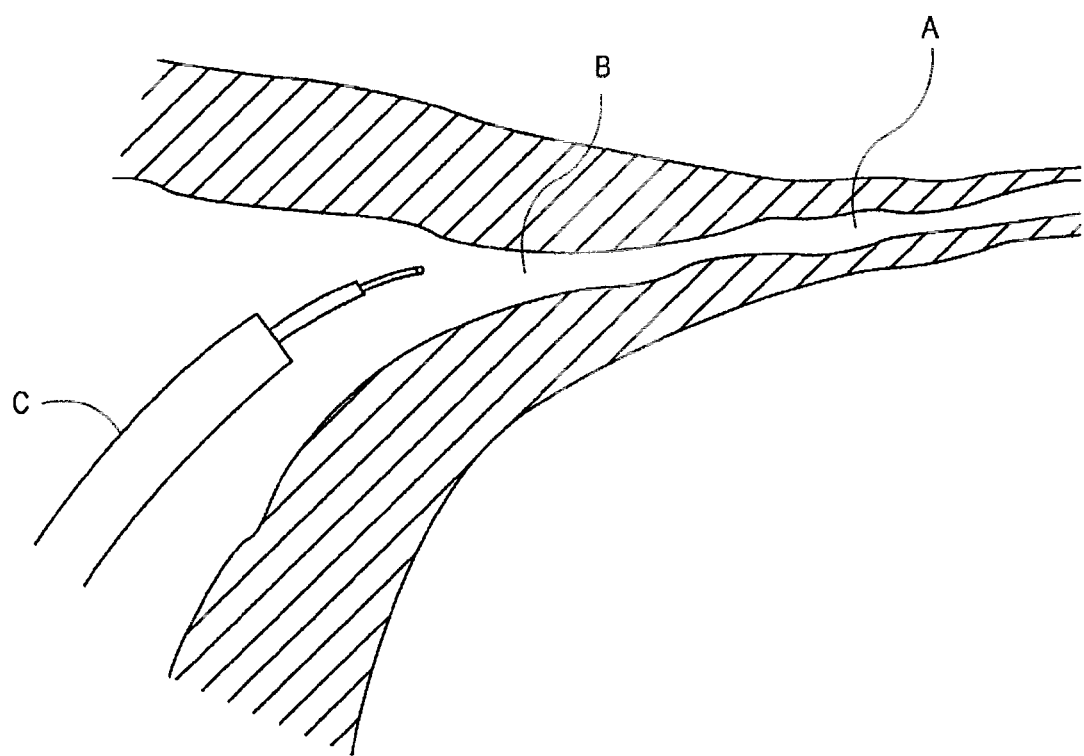
FIG. 13a shows an endoscope approaching the ostium of a fallopian tube in a cross sectional view.

FIG. 13*a* shows the approach of a delivery of a sterilization device 1300, which is a form of a contraceptive fallopian tube implant, inside a endoscope C into a fallopian tube A. The ostium section B is also shown.

FIG. 13*b* shows a sterilization device 1300 in an expanded configuration, which typically exists after the device 1300 has been deployed in a fallopian tube. The sterilization device 1300 includes an expandable outer coil 1302, an inner coil 1304, and polymer fiber 1306 such as PET to encourage tissue growth. One or both of the inner and outer coils may be constructed from a super elastic material, such as a Nickel-Titanium (Ni—Ti) alloy. The inner and outer coils may be coated with a layer of titanium oxide (TiO). A TiO coating will aid in biocompatibility and visibility of the sterilization device 1300. Heat treating a Ni—Ti causes a controlled layer of TiO to form, and different thicknesses of coating correspond to different color effects of the TiO. For example the inner and outer coils may be heat treated until a 60 nm TiO layer is present, upon which the inner and outer coils will give a bluish appearance which provides a contrast relative to a color of human reproductive organs.

FIG. 13*c* shows the sterilization device 1300 in a non-expanded configuration coupled to a delivery catheter 1308. The delivery catheter 1308 includes an outer portion or catheter 1310, and inner portion or catheter 1312 (not shown), and a core wire 1314 (not shown). As shown, the black marker 1316 on the outer catheter 1310 may be first aligned with the ostium of the fallopian tube (not shown) under fluoroscopy.

FIG. 13*d* shows the sterilization device 1300 in a non-expanded configuration coupled to a delivery catheter 1308. The outer catheter 1310 is withdrawn at the proximal part of the catheter 1308 exposing the expandable outer coil 1302 while fully wound down in a non-expanded state. As shown in close-up view A-A a gold band 1318 on the inner catheter 1312 may be used to check alignment with the ostium, as the black marker 1316 is withdrawn with the outer catheter 1310. While the gold band 1318 remains aligned, a release wire 1320 coupled to the outer coil 1302 is pulled in the proximal direction to expand the outer coil 1302.

FIG. 13*e* shows the sterilization device 1300 in an expanded configuration coupled to a delivery catheter 1308. The device 1300 remains attached to the core wire 1314 at the inner coil 1304. The core wire is withdrawn to fully disengage the device 1300.

Figure 13F:
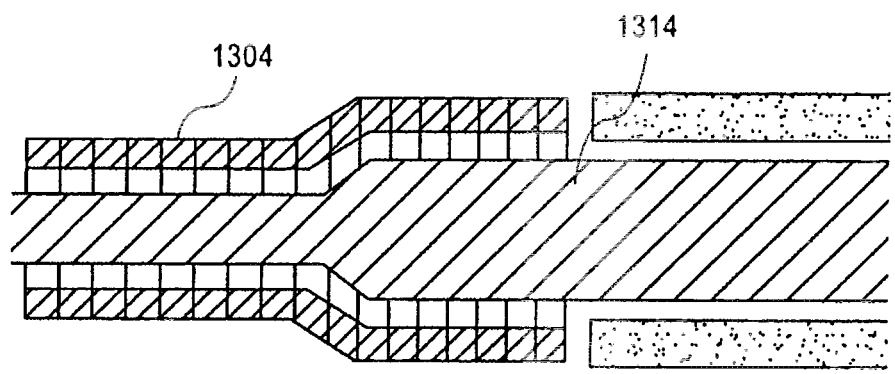
FIG. 13f is a cross sectional view of a sterilization device coupled to a delivery catheter by an interference fit.

FIG. 13*f* shows a magnified cross sectional view of the core wire 1314 and inner coil 1304 interference fit before disengagement. The inner coil 1304 is expanded over the core wire 1314 to provide a frictional interference fit. The interference fit allows the device to be disengaged in an axial movement with the endoscope and delivery catheter remaining in a stable position and without requiring rotation of the endoscope and the delivery catheter as a unit and without requiring rotation of the delivery catheter relative to the endoscope. No radial torque is required as opposed to the devices in U.S. Pat. No. 6,526,979 and U.S. Pat. No. 6,634,361. This is beneficial as alignment with the fallopian tube is easily maintained when the endoscope, delivery catheter and any additional stabilization device is not rotated and thus remain in a rotationally stable position relative to a patient. Further, the operator may need to use only a rotary knob or thumbwheel to release the sterilization device from the delivery catheter. The interference fit is also more reliable in disengagement and detachment than a fit which requires a radial torque, for example by eliminating interference between PET fibers and the core wire which develop from radial movement.

Figure 13G:
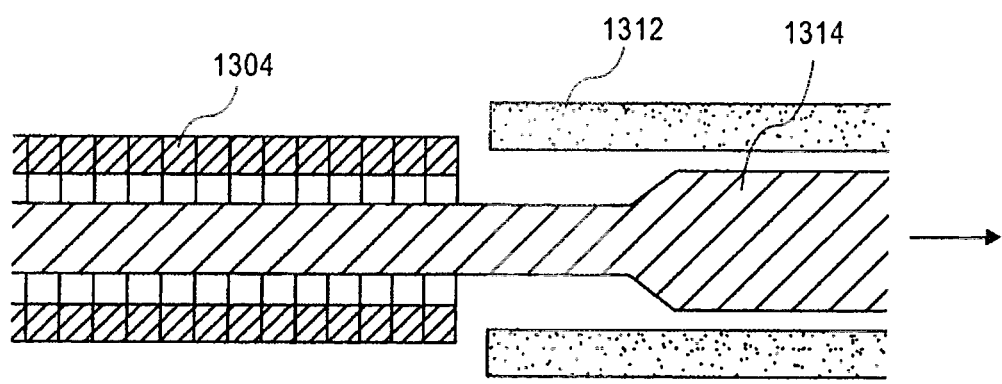
FIG. 13g is a cross sectional view of a sterilization device uncoupled from a delivery catheter.

FIG. 13*g* shows a magnified cross sectional view of the core wire 1314 and inner coil 1304 interference fit after disengagement. The core wire 1314 is withdrawn from the inner coil 1304 to disengage the device 1300. The inner catheter 1312 remains stationary to buttress against the inner coil 1304 while the core wire 1314 is being withdrawn. After the core wire 1314 is disengaged, the entire delivery catheter 1308 may be withdrawn from the patient.

Figure 13H:
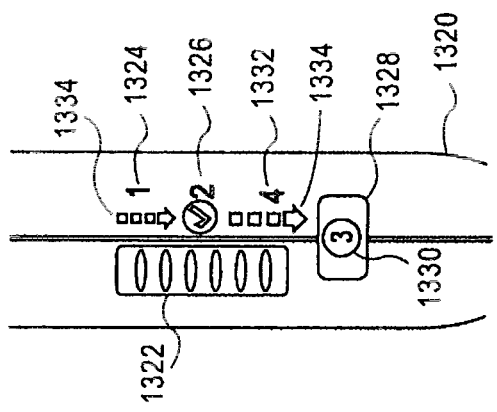
FIG. 13h shows a portion of a top view of a handle.

FIG. 13*h* shows a portion of a top view of a handle 1320 of a sterilization device 1300. The handle 1320 includes a thumbwheel 1322 at an initial position. The handle 1320 includes a second thumbwheel position with a first indicator 1324. The first indicator 1324 functions as a visual reminder to an operator and refers to withdrawing the outer catheter 1310 by rotating the thumbwheel 1322 in a proximal direction until the thumbwheel 1322 stops, which exposes the expandable outer coil 1302 (this step is performed after previously aligning the black marker 1316 with the ostium). As shown the first indicator 1324 is labeled "1" to indicate a first operation, however other labels may be used to indicate a first operation, for example "A". The first indicator 1324 may be imprinted onto, or molded into the handle 1320.

The handle 1320 includes a second position with a second indicator 1326. The second indicator 1326 functions as a visual reminder to the operator to check alignment of the gold band 1318 on the inner catheter 1312 with the ostium, as the black marker 1316 has been withdrawn with the outer catheter 1310. As shown the second indicator 1326 is labeled "2" and includes a check mark to indicate a second operation, however other labels may be used to indicate a second operation, for example "B" or a check mark alone or a combination thereof. The second indicator 1326 may be imprinted onto, or molded into the handle 1320.

The handle 1320 includes a safety button 1330 with a third indicator 1328. The third indicator 1328 functions as a labeled operation for pressing the safety button. The safety button 1330 is pressed after checking alignment with of the gold band 1318 with the ostium. Pressing the safety button 1330 allows thumbwheel to travel to a second position and allows the operator to proceed to the next operation of delivery. As shown the third indicator 1328 is labeled "3" to indicate a third operation, however other labels may be used to indicate a third operation, for example "C". The third indicator 1328 may be imprinted onto, or molded into the safety button 1330.

The handle 1320 includes a final thumbwheel position with a forth indicator 1328. The forth indicator 1332 functions as a visual reminder to an operator and refers to rotating the thumbwheel 1322 until it stops, which pulls the release wire 1320 coupled to the outer coil 1302 to expand the outer coil 1302 and also withdraws the core wire 1314 from the inner coil 1304 to fully disengage the device 1300. As shown the forth indicator 1328 is labeled "4" to indicate a forth operation, however other labels may be used to indicate a forth operation, for example "D". The forth indicator 1328 may be imprinted onto, or molded into the handle 1320.

The handle 1320 may also include arrow marks 1334 to indicate the direction of thumbwheel travel, which as shown is a proximal direction away from the patient. The arrow marks 1334 may be imprinted onto, or molded into the handle 1320. Alternatively the indicators 1324, 1326, 1328, 1332 and arrow marks 1334 may incrementally glow or incrementally light up via powered LED lights to indicate to the operator which operations have been performed in the delivery of the sterilization device 1300. This is advantageous as it allows the operator to know which operation have been performed if the operator has deviated attention from the delivery of the sterilization device 1300. Alternatively an audible signal may work in lieu of or in conjunction with the indicators. The audible signal may have different tonality for each indicator, or use a recorded or electronically generated voice signal (e.g. at indicator 1332 a signal stating "CHECK"). The handle would include a power source such as a battery for lights or audible signals. Alternatively the handle may include a wireless transmitter which transmits one or more analog or digital electronic signals to an external device. The external device would be capable if processing the signal in to an audible signal and/or a visual signal, for example a flashing light on a set-top box, a speaker on a set-top box, or a visual cue digitally overlaid on a television screen currently projecting the procedure. The handle may use an analog radio frequency signal or wireless data connection such as a WiFi (IEEE 802.11a or b or g standard) connection or a Bluetooth wireless connection or a wireless USB connection or other WPAN (Wireless Personal Area Network) connection standards.

Figure 13I:
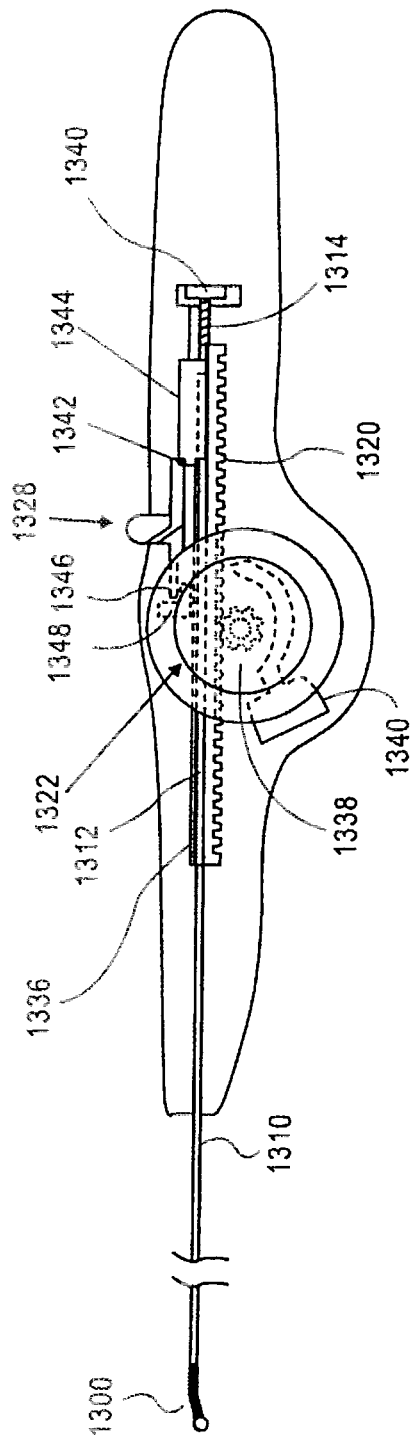
FIG. 13i shows an internal side view of a handle.

FIG. 13*i* shows an internal side view of one side of the handle 1320. The handle 1320 also includes an opposite side which is not shown. The handle includes the thumbwheel 1322 which includes a gear 1338 shown in hidden lines. The slideable outer catheter 1310 is coupled to a rack 1336, the stationary inner portion or catheter 1312 resides within the outer portion or catheter 1310 and is coupled to the handle 1320, and the core wire 1314 resides slideably within the inner catheter 1312 and is coupled to a slideable core wire holder 1340. The gear 1338 meshes with the rack 1336 and thus may move the outer catheter 1310. When the thumbwheel is rotated clockwise from an initial position, movement of the gear 1338 causes the rack 1336 to travel in a proximal direction away from the sterilization device 1300. The thumbwheel 1322 and rack 1336 have three incremented positions, not including positions traveling between, which is an initial position where the sterilization device 1300 is at least partially covered by the outer catheter 1310, a second position where the outer catheter 1310 has withdrawn to expose the sterilization device 1300, and a final position where the sterilization device is released. As shown the thumbwheel 1322 and rack 1336 are in the second position. A detent mechanism 1340 shown in hidden lines allows the rack 1336 to ratchet only in the proximal direction.

As shown the thumbwheel 1322 and rack 1336 are in the second position. The safety button includes a pivot 1342 where the safety button 1328 hinges upon the handle 1320. As shown the rack 1336 is in contact with the safety button 1328, thus when the safety button is not depressed the rack 1336 cannot travel farther. The rack 1336 is stopped by the most proximal position 1346 of the safety button 1328 which blocks the rack 1336. At the most distal position 1346 of the safety button, shown in hidden lines, the safety button is kept from depressing by a standoff 1348, shown in hidden lines. Pressing the safety button causes the most distal portion 1346 to travel in the counter clockwise direction about the pivot 1342 and elastically deform the standoff 1348. After the most distal portion 1346 passes by the standoff 1348, the standoff 1348 will return to its original position and thereby block the most distal portion 1346 from traveling back into the clockwise direction. Pressing the safety button 1328 also causes the most distal portion 1344 of the safety button 1328 to travel counter clockwise about the pivot 1342 and thus raise above and allow the rack 1336 to travel in the proximal direction.

After the safety button is depressed, the rack 1336 is free to travel in the proximal direction. Continued proximal travel of the rack by clockwise rotation of the thumbwheel 1322 will cause the rack to contact the slideable core wire holder 1340 (to which the core wire 1314 is coupled to) and in turn cause the core wire 1314 and the release wire 1320 (not shown) to move in the proximate direction and to ultimately release the sterilization device 1300 when the rack reaches the final position.

Figure 14:
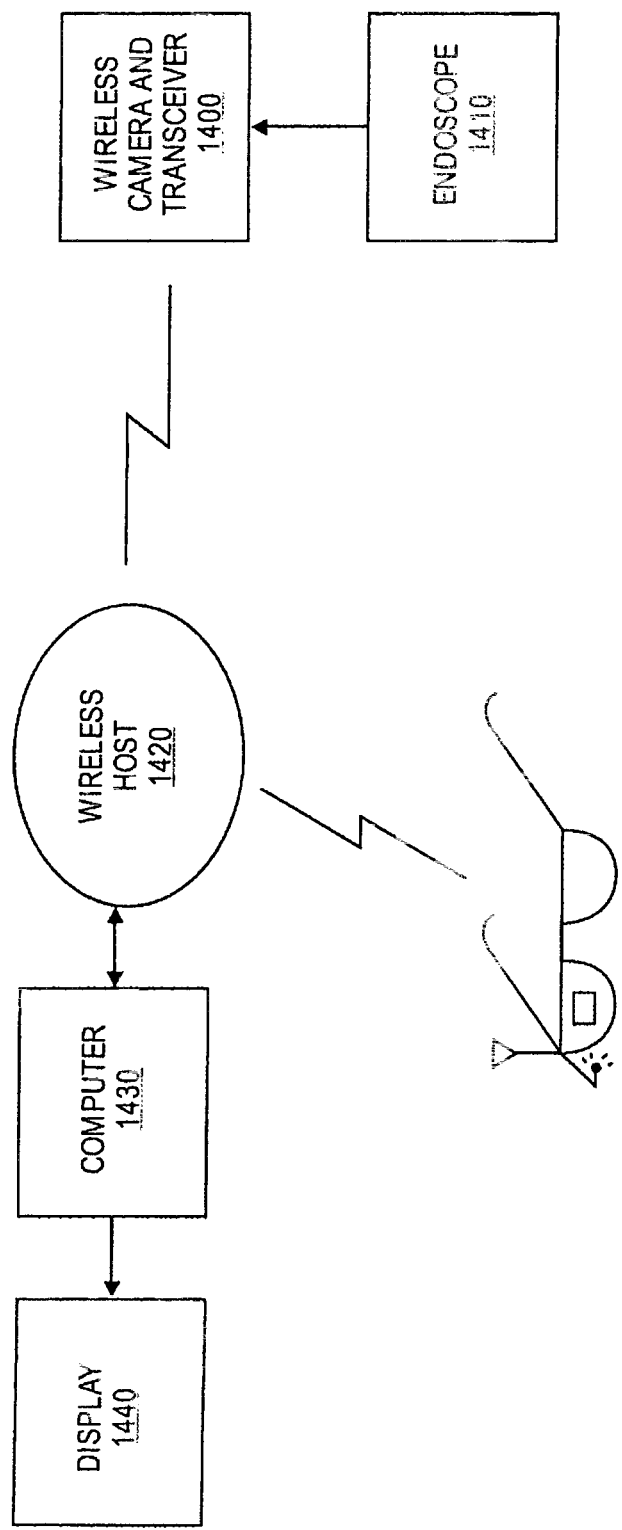
FIG. 14 is a schematic for a wireless camera system using an endoscope.

FIG. 14 shows a system for a wireless endoscope. A wireless camera 1400 integrated into or connected onto a endoscope 1410 transmits a wireless camera signal to a wireless host controller 1420. The wireless host 1420 may be controlled by a computer 1430 which receives and transmits the camera signal to a monitor 1440. The system may use a wireless data connection such as a WiFi (IEEE 802.11a or b or g standard) connection or a Bluetooth wireless connection or a wireless USB connection or other WPAN (Wireless Personal Area Network) connection standards. Alternatively the host controller 1420 may transmit a wireless signal to a secondary or alternative display 1450, such as a heads up display integrated into eye glasses or other headmounted displays. The wireless camera 1400 may serve as the host controller and transmit wireless signals to any display which can receive the signals.

Figure 15A:
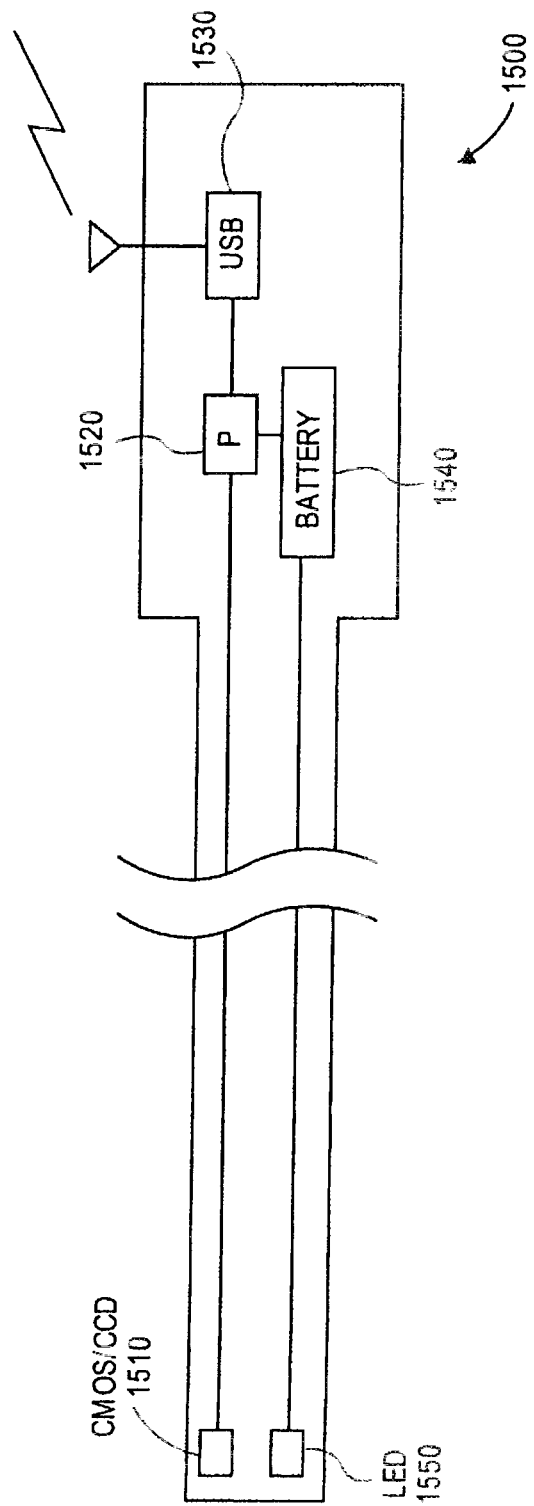
FIG. 15a is a schematic for a wireless endoscope.

FIG. 15*a* shows a schematic for a wireless endoscope 1500. A CMOS or CCD imaging sensor 1510 transmits a signal to a processor 1520 which in turn transmits the signal to a wireless transmitter 1530 mounted in a handle. The transmitter 1530 in turn transmits the signal to a system as shown in FIG. 14. The processor may also convert the signal into a viewable signal for direct transmission to a display. A battery 1540 powers a LED light source 1550 at the distal end of the endoscope. Alternatively a fiber optic light source may be used. The endoscope also includes elements not shown including hand controls and wires for manipulation and a working channel for inserting devices.

Figure 15B:
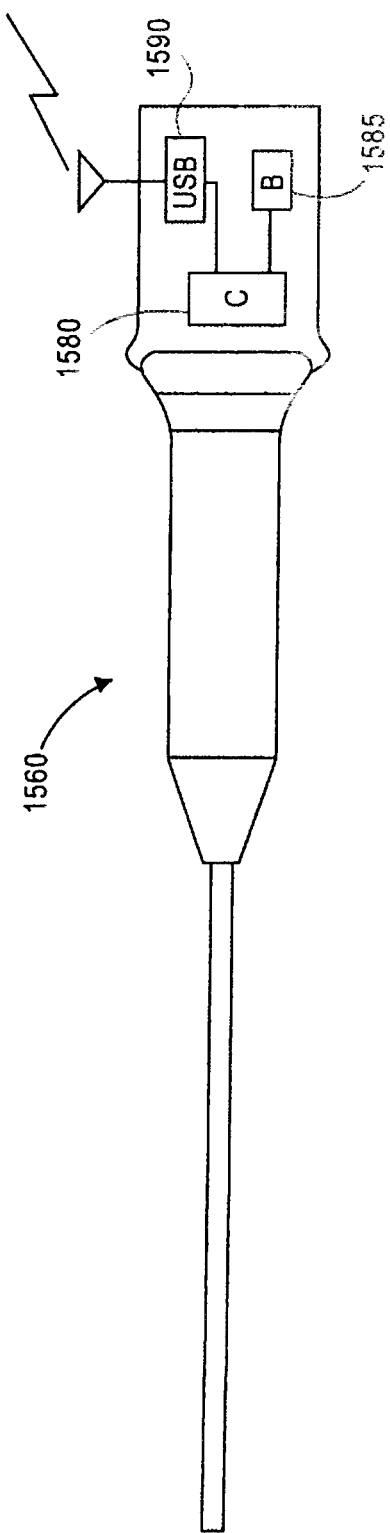
FIG. 15b is a schematic for a wireless camera which couples to a standard endoscope.

FIG. 15*b* shows a schematic for a wireless endoscope camera 1560. The camera 1560 may be used on standard fiberscopes. The camera 1560 mechanically couples to the eyepiece of an endoscope 1570. The camera 1560 includes a digital camera 1580, a battery 1585, and a transmitter 1590 to transmit signal to a system as shown in FIG. 14. Examples of standard sized fiberscopes for use in a minimally invasive method of sterilization include rigid scopes with a 5.5 mm outer diameter (O.D.), flexible scopes with a 4.0 mm O.D., both of which have at least a 5 french working channel, and range in length from 30-40 cm.

While the exemplary embodiment of the present invention has been described in some detail for clarity of understanding and by way of example, a variety of adaptations, changes and modifications will be obvious to those who are skilled in the art. Hence the scope of the present invention is limited solely by the following claims.

We claim:

1. A medical device for a transcervical medical sterilization procedure, comprising:
   an elongated catheter with a distal portion and a proximal portion;
   a fallopian tube implant removably coupled to the distal portion;
   a handle coupled to the proximal portion;
   a rack within the handle, wherein the rack travels in a proximal direction within the handle and does not travel in a distal direction within the handle when the fallopian tube implant is coupled to the distal portion; and a release mechanism on the handle and operably coupled with the rack, wherein the release mechanism and rack are movable from an initial position until the release mechanism and rack stop at a final incremented position to removably decouple the fallopian tube implant from the elongated catheter, and the handle includes an indicator that illuminates upon moving the release mechanism and rack to the final incremented position to indicate that the fallopian tube implant is decoupled from the elongated catheter wherein the release mechanism comprises a thumbwheel that is rotatable from the initial position until the thumbwheel stops at the final incremented position.

2. The medical device of claim 1, wherein moving the release mechanism and rack to the final incremented position causes a core wire to withdraw from the fallopian tube implant.

3. The medical device of claim 2, further comprising an inner catheter within the elongated catheter, and the inner catheter buttresses against the fallopian tube implant while the core wire is withdrawn from the fallopian tube implant.

4. The medical device of claim 1, wherein the indicator is an LED light.

5. The medical device of claim 1, wherein the release mechanism and rack are movable from the initial position to a first incremented position and then to the final incremented position, and the handle additionally includes a first indicator that illuminates upon moving the release mechanism and rack to the first incremented position.

6. The medical device of claim 1, wherein the handle additionally includes a power source for illuminating the indicator.

7. The medical device of claim 1, wherein the handle additionally includes an audible indicator that makes an audible sound upon moving the release mechanism and rack to the final incremented position.

8. A medical device for a transcervical medical sterilization procedure, comprising:

an elongated catheter with a distal portion and a proximal portion;

a fallopian tube implant removably coupled to the distal portion;

a handle coupled to the proximal portion;

a rack within the handle, wherein the rack travels in a proximal direction within the handle and does not travel in a distal direction within the handle when the fallopian tube implant is coupled to the distal portion; and a release mechanism on the handle and operably coupled with the rack, wherein the release mechanism and rack are movable from an initial position until the release mechanism and rack stop at a final incremented position to removably decouple the fallopian tube implant from the elongated catheter, and the handle includes an indicator that makes an audible sound upon moving the release mechanism and rack to the final incremented position to indicate that the fallopian tube implant is decoupled from the elongated catheter wherein the release mechanism comprises a thumbwheel that is rotatable from the initial position until the thumbwheel stops at the final incremented position.

9. The medical device of claim 8, wherein moving the release mechanism and rack to the final incremented position causes a core wire to withdraw from the fallopian tube implant.

10. The medical device of claim 9, further comprising an inner catheter within the elongated catheter, and the inner catheter buttresses against the fallopian tube implant while the core wire is withdrawn from the fallopian tube implant.

11. The medical device of claim 8, wherein the indicator emits at least a single tone.

12. The medical device of claim 8, wherein the indicator emits a spoken voice.

13. A medical device for a transcervical medical sterilization procedure, comprising:

an elongated catheter with a distal portion and a proximal portion;

a fallopian tube implant removably coupled to the distal portion;

a handle coupled to the proximal portion;

a rack within the handle, wherein the rack travels in a proximal direction within the handle and does not travel in a distal direction within the handle when the fallopian tube implant is coupled to the distal portion; and a release mechanism on the handle and operably coupled with the rack, wherein the release mechanism and rack are movable from an initial position until the release mechanism and rack stop at a final incremented position to removably decouple the fallopian tube implant from the elongated catheter, and the handle includes a wireless transmitter for transmitting a signal upon moving the release mechanism and rack to the final incremented position to indicate that the fallopian tube implant is decoupled from the elongated catheter wherein the release mechanism comprises a thumbwheel that is rotatable from the initial position until the thumbwheel stops at the final incremented position.

14. The medical device of claim 13, wherein moving the release mechanism and rack to the final incremented position causes a core wire to withdraw from the fallopian tube implant.

15. The medical device of claim 14, further comprising an inner catheter within the elongated catheter, and the inner catheter buttresses against the fallopian tube implant while the core wire is withdrawn from the fallopian tube implant.

16. The medical device of claim 13, further comprising a separate instrument to receive the signal and trigger a visual or audible indicator.

* * * * *